(12) United States Patent
Gruber et al.

(10) Patent No.: US 7,531,717 B2
(45) Date of Patent: May 12, 2009

(54) REGULATORY GENES INVOLVED IN CONDENSED TANNIN SYNTHESIS IN PLANTS

(75) Inventors: Margaret Y. Gruber, Saskatoon (CA); Heather Ray, Saskatoon (CA)

(73) Assignee: Agriculture and Agri-Food Canada (CA)

( * ) Notice: Subject to any disclaimer, the term of this patent is extended or adjusted under 35 U.S.C. 154(b) by 360 days.

(21) Appl. No.: 10/352,773

(22) Filed: Jan. 28, 2003

(65) Prior Publication Data

US 2004/0006793 A1 Jan. 8, 2004

Related U.S. Application Data

(63) Continuation of application No. PCT/CA01/01091, filed on Jul. 27, 2001.

(60) Provisional application No. 60/221,560, filed on Jul. 28, 2000.

(51) Int. Cl.
*C12N 15/29* (2006.01)
*C12N 15/82* (2006.01)
*A01H 5/00* (2006.01)
*A01H 5/10* (2006.01)

(52) U.S. Cl. ........................ 800/282; 800/298; 800/306; 800/312; 536/23.1; 536/23.6; 435/419

(58) Field of Classification Search ................ 536/23.1, 536/23.6; 800/282, 287, 298, 312; 435/320.1, 435/419
See application file for complete search history.

(56) References Cited

FOREIGN PATENT DOCUMENTS

| WO | WO-93/14211 | 7/1993 |
|---|---|---|
| WO | WO-98/07836 | 2/1998 |

OTHER PUBLICATIONS

Damiani F. et al. Aust. J. of Plant Physiology; 1999, vol. 26; pp. 159-169.*
Bradley J. et al. Plant Science; 1999, vol. 140, pp. 31-39.*
Baudry A. et al. The Plant Journal, 2004; vol. 39, pp. 366-380.*
Damiani, F.,et al. ,"The maize transcription factor Sn alters proanthocyanidin synthesis in transgenic *Lotus corniculatus* plants", *Aust. J.Plant Physiol.*, 26, (1999),pp. 159-169.

* cited by examiner

*Primary Examiner*—Russell Kallis
(74) *Attorney, Agent, or Firm*—Schwegman, Lundberg & Woessner, P.A.

(57) ABSTRACT

The present invention provides two novel regulatory genes and encoded proteins which can be used to alter the biosynthesis and accumulation of condensed tannin levels in plants and plant tissues. The present invention further encompasses transgenic constructs containing the novel regulatory genes herein referred to as Ulimyc, Corniculmyc and Japmyc, for use in the transformation of plants and plant tissues and transgenic plants containing such constructs. The identification and characterization of these novel genes provide a mechanism for altering tannin production in plants and allows one to alter such levels to produce a variety of benefits in the field of agriculture, land reclamation animal farming and food technology in general.

29 Claims, 6 Drawing Sheets

Supplementary Fig. 1 Part 1

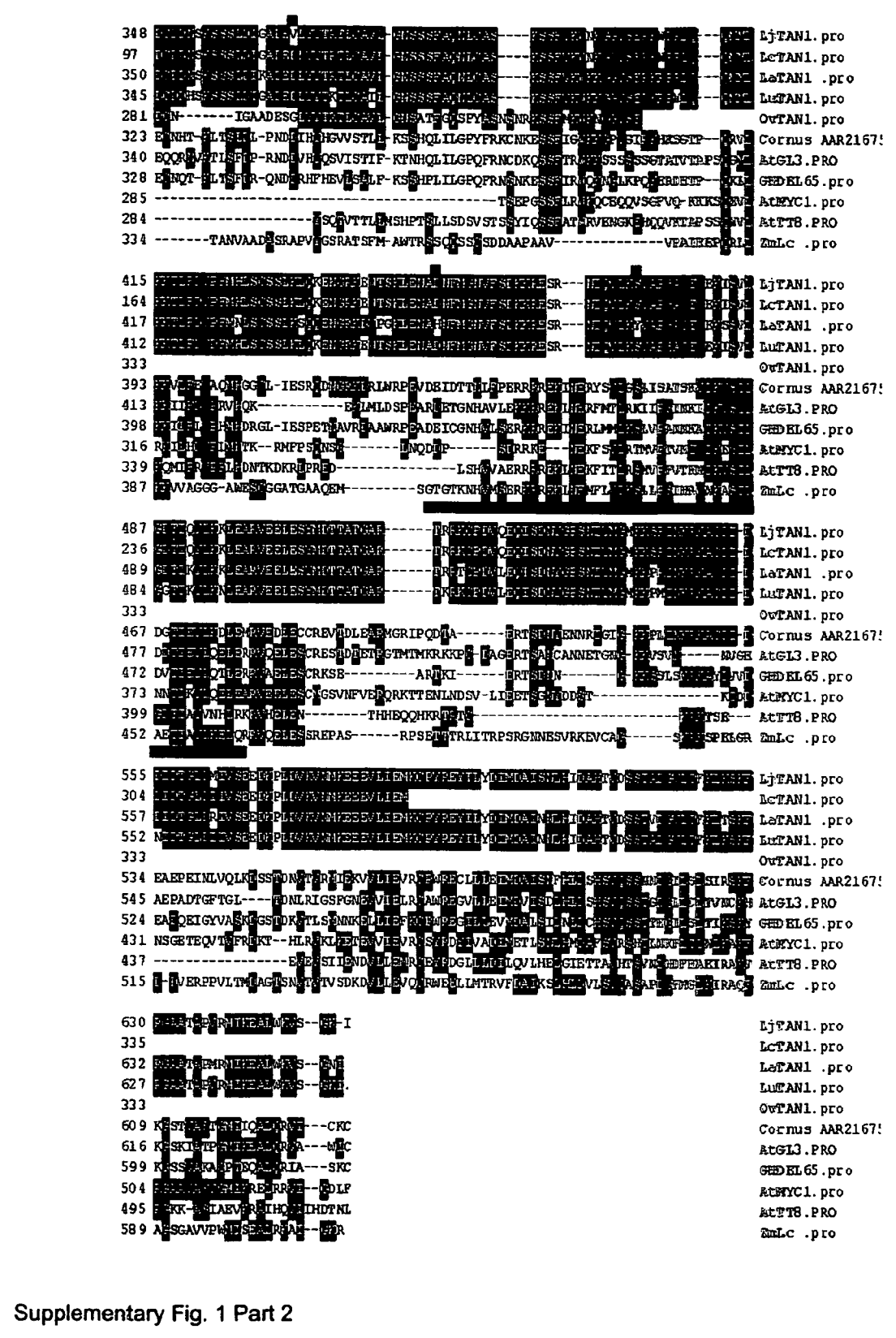

Supplementary Fig. 1 Part 2

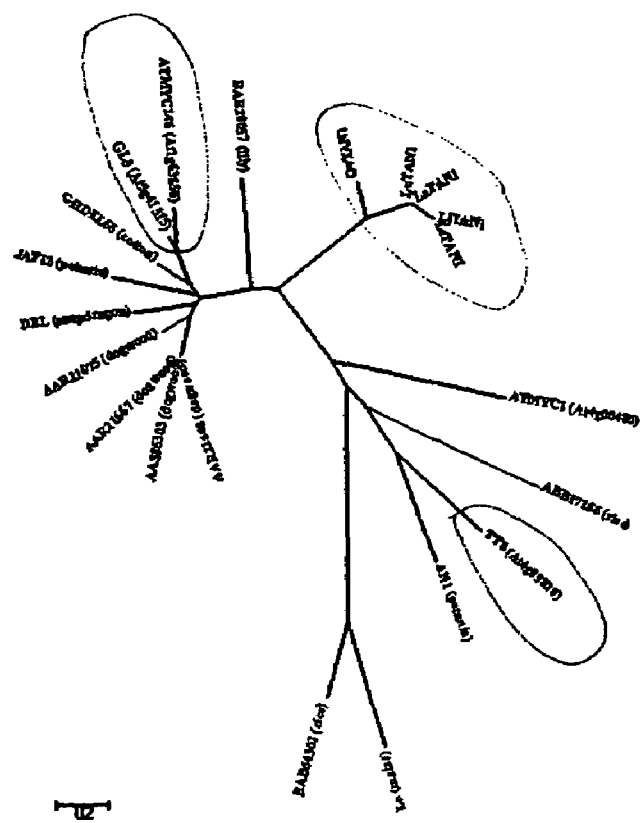
Fig. 2. Phylogenetic tree of TAN1 and its homologues

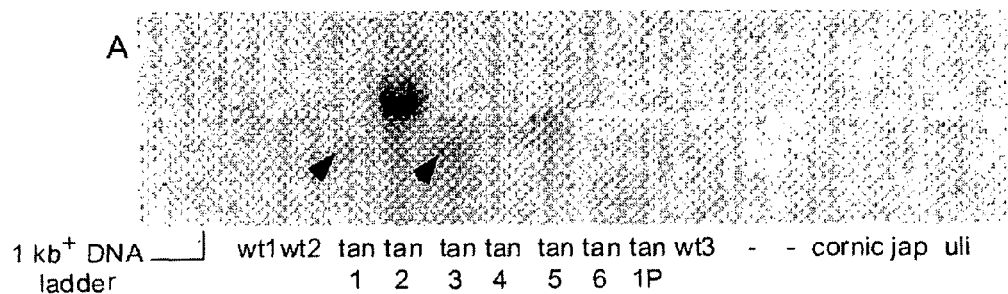
FIG. 5A
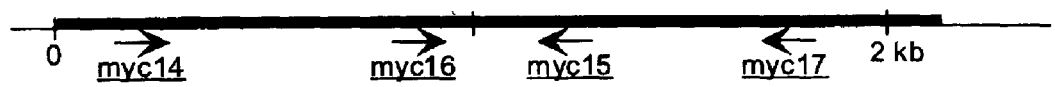
FIG. 5B
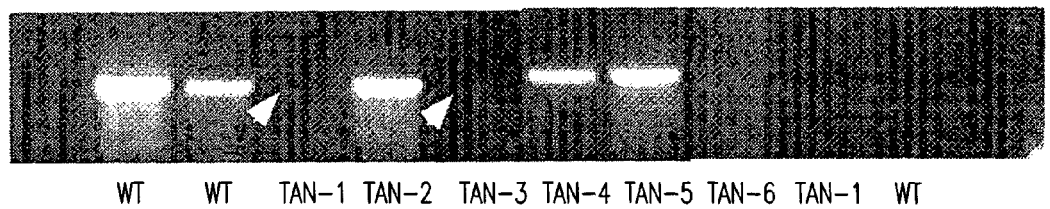
FIG. 5C
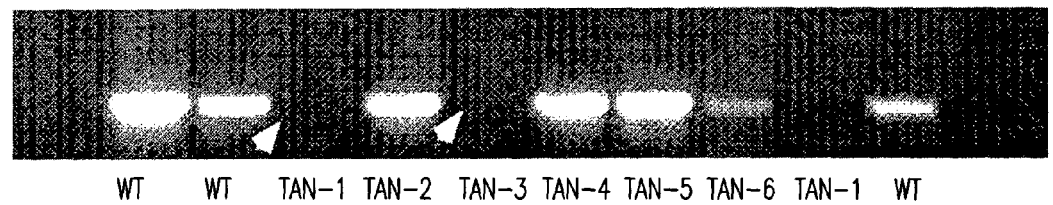
FIG. 5D
FIG. 5E    FIG. 5F    FIG. 5G

REGULATORY GENES INVOLVED IN CONDENSED TANNIN SYNTHESIS IN PLANTS

RELATED APPLICATIONS

This application is a continuation under 35 U.S.C. 111(a) of PCT/CA01/01091 filed Jul. 27, 2001 and published in English as WO 02/10412 A2 on Feb. 7, 2002, which claims priority from U.S. Provisional Patent Application No.: 60/221,560, filed on Jul. 28, 2000, which application and publication are incorporated herein by reference.

FIELD OF THE INVENTION

The present invention relates to regulatory genes and encoded proteins from *Lotus uliginosis, Lotus japonicus* and *Lotus corniculatus* which can be used to alter the biosynthesis and accumulation of condensed tannin levels in plants and plant tissues. The present invention further relates to transgenic constructs containing the novel regulatory genes and methods for making such, for use in the transformation of plants and plant tissues, and to transgenic plants containing such constructs.

BACKGROUND OF THE INVENTION

Condensed tannins (also called proanthocyanidins) are plant phenolic compounds which are structurally related to the anthocyanins that cause purple and red colours in flowers. Specifically, condensed tannins are 1,4-linked and 1,6-linked polymers of flavan-4-ols, derived by condensation from several products of the phenylpropanoid/flavonoid pathway (FIG. 1) (Gruber et al., 1999; Peterson et al., 1999). The biosynthesis of these two classes of compounds, i.e., tannins and anthocyanins, occurs in plants using a set of common genes, after which the pathway diverges and unique genes are required for each class. Many plant species accumulate condensed tannins in their vegetative, floral and seed tissues (Porter 1988). Legumes are a particularly rich source of these compounds. The legumes sainfoin (*Onobrychis viciifolia*) and big trefoil (*Lotus uliginosis*) contain substantial levels of condensed tannins in leaf and other vegetative tissue and in seed coats. With the exception of barley and sorghum seedcoats (Butler 1982; Erdal 1986) and one report in rice (Reddy et al., 1995), the major cereal crops do not express condensed tannins. Several other species such as alfalfa, white clover, *L. japonicus* and the oilseed *Brassica*, only express condensed tannins in seedcoats.

The biological properties of tannins are related to their chemical structure. Their polymeric phenol nature facilitates hydrogen bonding with proteins in preference to other molecules (Hagerman and Butler 1981). The combination of hydroxyl groups (which can easily ionize to form quinone) with the ortho position of hydroxyl groups on ring B (which facilitates metal binding), contribute to their antioxidant properties and their ability to protect from excess sunlight. Alfalfa (lucerne; *Medicago sativa* or *M. falcata*) produces a linear procyanidin (3'4'-OH) condensed tannin polymer in the testa layer of the seedcoat as well as several smaller secreted flavonoids, while the leaves normally produce flavone glycosides instead of tannins (Koupai et al., 1993; Olah and Sherwood, 1971; Saleh et al., 1982). Chalcone synthase (CHS) and dihydroflavonol reductase (DFR) are inconsistently expressed in alfalfa leaves, while the flavanone 3B-hydroxylase (F3H) gene is not detected at all in alfalfa leaves (Charrier et al., 1995; Junghans et al., 1993; Skadhauge et al., 1997); Ray and Gruber unpublished).

Leucoanthocyanidin reductases (LARs) comprise the first step committed exclusively to condensed tannins in the flavonoid pathway. LARs are normally expressed only in tannin-containing tissue (Skadhauge, 1996; Koupai-Abyazani et al., 1993; Singh et al., 1997; Joseph et al., 1998). In alfalfa, LCR (3'4'-OH-specific LAR) activity is high only during early seed development, but cannot be detected in leaves (Skadhauge et al., 1997). The flavanone 3B-hydroxylase gene (F3I) and 3'4'-OH-specific leucoanthocyanidin reductase gene (LCR) are two functional blocks that prevent alfalfa leaves from accumulating condensed tannins.

Natural and induced mutants affecting condensed tannin or anthocyanin expression in various crop and forage plant species have been identified, including sorghum, barley, pea, *Arabidopsis*, rice and *Lotus japonicus* (Butler et al. 1982; Gruber et al. 1996; Jende-Strid 1993, 1990; Koorneef et al. 1982; Koorneef 1991; Jambunathan et al. 1986; Reddy et al. 1995). However, no mutations or variants with leaf tannin have been found in alfalfa or related *Medicago* species (Goplen et al., 1980). A somaclonal variant of alfalfa with a small but detectable content of leaf bud flavan-3-ol was recovered (Lees et al., 1992), but tannin could not be extracted from the buds and the trait proved unstable. Somatic hybridization between sainfoin and alfalfa has been used to develop alfalfa-like hybrids with sainfoin DNA, but to date no plants have been recovered with stable leaf tannin contents (Larkin et al., 1998). Several of the diploid *Medicagos* synthesize anthocyanins that are visible as a small red patch on developing and mature leaves. Alfalfa only accumulates anthocyanins in senescing leaves, although rare germplasm with small red leaf sectors has been discovered in a breeding program at the University of Wisconsin.

Some forage legume species express condensed tannins in leaves and other vegetative tissues. These include sainfoin, big trefoil (*L. uliginosis*), *L. angustissimus*, all of which express high levels of leaf condensed tannins. Birdsfoot trefoil (*L. corniculatus*) expresses leaf condensed tannin at a moderate level, while the related *L. japonicus* does not express leaf condensed tannin. All of these express condensed tannin in seed coat (Gruber et al., 1999).

Barley produces condensed tannin in the testa layer of seed coat; a series of mutants lacking condensed tannin preduction has been developed (Jende-Strid 1993). In one case, the mutation has been complemented by transient expression of the DFR gene and by DNA sequencing (Olson et al., 1993; Wang et al., 1993). Another of these mutants, ant 13, has been suggested as a regulatory gene.

The alteration of various intermediates in the phenylpropanoid/flavonoid pathway in certain plants has been demonstrated or suggested to be advantageous for certain uses. For example, certain flavonoids have been suggested to have the ability to inhibit phytopathogens in certain plant species. Flavonoid levels have been manipulated in order to select particular flower colours and patterns. Moreover, increased amounts of condensed tannins in forage crops have been found to be useful for decreasing bloat in cattle and improving ruminal protein bypass.

Several researchers have focused on the alteration of the flavonoid pathway in order to manipulate condensed tannin synthesis in plants. Variations in the ability to affect changes in anthocyanin and condensed tannin expression have been observed using the maize C1gene (myb-like) and combinations of myc-like genes constitutively expressed in maize, *Arabidopsis*, chrysanthemum, tomato, petunia, and oats (Lloyd, 1992; Cone et al., 1986; Paz-Arez et al., 1987; Wong et al., 1991; Bradley et al., 1998). For example, B-Peru, Lc (myc-like) and C1 anthocyanin regulatory genes were expressed in white clover, peas, *Arabidopsis*, petunia, wheat, barley, oats, and *Brassica napus* and stimulated anthocyanin production in leaves (Lloyd et al., 1992; Wong et al., 1991; de Majnik et al., 1998;Bradley et al., 1998;Babwah et al., 1998). The maize anthocyanin regulatory gene, Sn (myc-like) has been introduced into birdsfoot trefoil (*Lotus corniculatus*) and caused hairy root cultures to become pigmented (Damiani et al., 1998). Unexpectedly, condensed tannins and tannin genes, which are normally elevated in leaves of *Lotus corniculatus*, were either completely suppressed or unaffected in transgenic plants with the Sn gene, while root tannin levels were elevated (Damiani et al., 1999).

PCT/AU97/00529 is directed to nucleic acids and their encoded polypeptides involved in condensed tannin biosynthesis and their use in regulating the biosynthesis and accumulation of condensed tannins in plants. The nucleic acids are believed to encode leucoanthocyanidin reductases of plants and are stated to be useful in the production of bloat-safe forage crops and other crops with altered nutritional value, increased disease and pest resistance or improved malting qualities.

PCT/BG93/00019 is directed to a method for regulating the expression of one or more anthocyanin pigment genes in a plant. PCT/CA99/00056 is directed to methods and compositions for the alteration of compounds produced by secondary metabolic pathways in plants. Canadian patent application 2,130,800 is directed to a nucleotide sequence encoding flavonoid-3',5'-hydroxylase activity to alter pigment patterns in a transformed plant. PCT/EP99/00419 is directed to the use of transcription factor genes for flavonoid biosynthesis in order to manipulate the production of flavonoids other than anthocyanins in plants.

PCT/US98/12917 is directed to a method of producing resistance to plant microbial pathogens in the seeds of monocot plants using a chimeric DFR gene under the control of a testa-induced promoter. The patent application discloses a clone hypothesized to be a testa-specific gene from barley that is thought to be involved in the anthocyanidin and the condensed tannin pathway. However, neither gene promoter nor regulatory sequence was specifically isolated or characterized.

Identification of the genes regulating the synthesis of condensed tannins in plants would provide a means of manipulating the tannin levels of plants advantageously. Such genes could be used, for example, to develop alfalfa with leaves containing moderate condensed tannin levels for improved forage quality, as well as for the development of condensed tannins in canola vegetative tissues to provide insect resistance.

SUMMARY OF THE INVENTION

In accordance with the present invention are a group of regulatory genes that share significant sequence homology and affect the phenylpropanoid/flavonoid pathway to result in changes in the production of condensed tannins and anthocyanins in plant cells and tissues.

In accordance with an aspect of the present invention are three novel tannin regulatory genes, isolated from *Lotus uliginosis, Lotus japonicus* and *L. corniculatus* which can be used to alter condensed tannin levels in plant tissues. These genes are designated herein "Ulimyc", "Japmyc" and "Corniculmyc", respectively.

The partial genomic DNA sequence of the Ulimyc gene is shown in Table 1 (Sequence ID No: 1). Its encoded amino acid sequence (Sequence ID No: 7) is shown in Table 5. The complete Ulimyc cDNA sequence is shown in Table 2 (Sequence ID No:2). The substantially entire genomic DNA sequence of the Japmyc gene is shown in Table 3 (Sequence ID No: 3) and portions of its encoded amino acid sequence (Sequence ID No: 4, 5 and 6) is shown in Table 4. The partial genomic DNA sequence of Corniculmyc is shown in Table 6 (Sequence ID No: 8) and portions of the encoded amino acid sequence (Sequence ID No: 9 and 10) is shown in Table 7.

Japmyc or its homologue was expressed strongly in young leaf of *L. uliginosis, L. angustissimus* and sainfoin, all of which accumulate substantial amounts of condensed tannin in leaves (FIG. 2). It was expressed weakly in *L. corniculatus*, and appeared to be absent from young leaf of alfalfa and *L. japonicus* (FIG. 2). The level of expression seen in these plants strongly corresponded with their levels of condensed tannin production). Ulimyc is highly homologous to Japmyc and is strongly expressed in leaf of *L. uliginosis*.

Because of their regulatory function, Ulimyc, Japmyc and Corniculmyc can be used either for raising or lowering condensed tannin levels in different plants and plant tissues. The term "plant" includes whole plants, plant organs (e.g., leaves, stems, flowers, roots, etc.), seeds and plant cells and progeny of same. The class of plants which can be used in the methods of the invention are any plant that which expresses any of the genes of the phenylpropanoid/flavonoid pathway.

These manipulations may be accomplished using plant transformation and sense or antisense constructs of the gene under suitable promoters, depending on the application. The availability of tannin-related regulatory genes opens up a broad range of plant species to the manipulation of tannins for several different applications.

The Ulimyc, Japmyc and Corniculmyc genes each appear to encode a regulatory protein of the basic-helix-loop-helix class, with a degree of homology to known proteins of this class such as the delila protein of *Antirrhynum majus*.

In accordance with one embodiment of the invention, an isolated nucleic acid comprises a nucleotide sequence encoding a protein which is capable of increasing synthesis of condensed tannins in a plant.

According to one aspect of the invention is an isolated nucleic acid comprising:
 (a) the nucleotide sequence of Table 1 (SEQ ID NO: 1);
 (b) the nucleotide sequence of Table 2 (SEQ ID NO: 2);
 (c) the nucleotide sequence of Table 3 (SEQ ID NO: 3);
 (d) the nucleotide sequence of Table 6 (SEQ ID NO: 8);
 (e) a nucleotide sequence capable of hybridizing under stringent conditions with the nucleotide sequence of SEQ ID NO: 1, 2, 3, or 8.

The nucleic acids of the invention include DNA, genomic DNA, cDNA, RNA, mRNA and fragments or portions of the disclosed nucleotide sequences.

In accordance with a further embodiment, an isolated nucleic acid comprises an antisense nucleotide sequence which is capable of decreasing synthesis of condensed tannins in a plant.

According to another aspect of the present invention is an isolated nucleic acid comprising an antisense nucleotide sequence selected from the group consisting of:
 (a) the antisense strand of the nucleotide sequence of Table 1 (SEQ ID NO: 1);
 (b) the antisense strand of the nucleotide sequence of Table 2 (SEQ ID NO: 2);
 (c) the antisense strand of the nucleotide sequence of Table 3 (SEQ ID NO: 3);
 (d) the antisense strand of the nucleotide sequence of Table 6 (SEQ ID NO: 8);

(e) a nucleotide sequence capable of hybridizing under stringent conditions with the antisense strand of the nucleotide sequence of SEQ ID NO 1, 2, 3 or 8.

The invention further includes nucleic acid constructs, vectors and host cells containing the isolated nucleic acids described above.

The novel genes of the present invention can be used in genetic constructs and vectors useful for transforming plant cells and plant tissues in order to generate transgenic plants exhibiting altered levels of condensed tannins. Such plants may have additional nutritional compounds, altered secondary metabolic profiles, production of plants with modified taste, texture or appearance, production of plants with altered secondary metabolites involved in insect resistance or attraction, disease tolerance, forage quality or other biological processes that are influenced by the phenylpropanoid/flavonoid pathway leading to condensed tannin production. These genes can also be used in methods to identify other genes involved in the regulation of tannin biosynthesis as is understood by those skilled in the art.

The invention further includes an isolated nucleic acid comprising a nucleotide sequence having at least 50% sequence identity to the nucleotide sequences of Table 1 (SEQ ID NO: 1), Table 2 (SEQ ID NO:2), Table 3 (SEQ ID NO:3) or Table 6 (SEQ ID NO:8), preferably at least 60%, more preferably at least 70% or at least 80% and most preferably at least 90% to any of the aforementioned sequences.

In a preferred embodiment the invention further includes an isolated nucleic acid comprising a nucleotide sequence having at least 50% sequence identity to the nucleotide sequence of Table 2 (SEQ ID NO: 2), preferably at least 60%, more preferably at least 70% or at least 80% and most preferably at least 90% to SEQ ID NO: 2.

One skilled in the art would readily comprehend that nucleic acid sequence identity is the percentage of nucleotides in a candidate sequence that are identical with the nucleotides in the subject sequence when aligning the sequences. One skilled in the art would also readily be able to determine the parameters for aligning such sequences and use any appropriate algorithms and computer software in order to achieve the maximal alignment of sequences over their entire length.

The invention also includes polynucleotides which are complementary to the disclosed nucleotide sequences, polynucleotides which hybridize to these sequences under moderate to high stringency conditions and polynucleotides which are degeneracy equivalents of these sequences. The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993).

The present invention further provides portions of the disclosed nucleic acid sequences which are useful as probes and PCR primers, for example for identification of homologous genes, or for encoding fragments, functional domains or antigenic determinants of the Ulimyc, Japmyc or Corniculmyc proteins or for encoding the Ulimyc, Japmyc or Corniculmyc proteins or active fragments thereof.

The invention also provides portions of the disclosed nucleotide sequences comprising about 9 consecutive nucleotides (for use as probes, for example) to nearly the complete disclosed nucleic acid sequences.

The invention provides isolated nucleotide sequences corresponding to at least 9 or 10, preferably at least 15 and more preferably at least 20 consecutive nucleotides of the nucleotide sequences disclosed or enabled herein or their complements.

In accordance with a further embodiment, the invention provides antisense molecules which may be used to-prevent or downregulate expression of a Ulimyc, Corniculmyc or Japmyc protein. Such antisense molecules can be synthesized by methods known to those skilled in the art The invention further includes polymorphisms and alternatively spliced versions of the disclosed Ulimyc, Corniculmyc or Japmyc genes and proteins wherein nucleotide or amino acid substitutions or deletions do not substantially affect the functioning of the gene or its encoded protein.

The invention also enables the identificaton and isolation of allelic variants or homologues of the described Ulimyc, Corniculmyc or Japmyc gene, and their corresponding proteins, using standard hybridization screening or PCR techniques.

In accordance with another embodiment, the invention provides alterations of the isolated Ulimyc, Corniculmyc or Japmyc sequences that may be used, for example, for expression and functional studies of the encoded protein(s) and protein fragment(s). The Ulimyc, Corniculmyc or Japmyc DNA and cDNA sequences can be altered using procedures such as restriction enzyme digestion, DNA polymerase fill-in, exonuclease deletion, terminal deoxynucleotide transferase extension, ligation of synthetic or cloned DNA sequences and site-directed in vitro mutagenesis, including site-directed sequence alteration using specific oligonucleotides together with PCR. The Ulimyc, Corniculmyc or Japmyc DNA and cDNA sequences may also be altered using site-specific recombination for example.

The invention further provides a substantially purified protein encoded by any one of the amino acid sequences of Table 4 (SEQ ID NO: 4, 5 or 6), Table 5 (SEQ ID NO: 7) or Table 7 (SEQ ID NO: 9 or 10).

The invention farther includes a substantially purified protein comprising an amino acid sequence having at least 50% amino acid identity to the amino acid sequences of Table 4 (SEQ ID NO: 4, 5 or 6), Table 5 (SEQ ID NO: 7) or Table 7 (SEQ ID NO: 9 or 10), preferably at least 60%, more preferably at least 70% or at least 80% and most preferably at least 90%.

In one preferred aspect the invention further includes a substantially purified protein comprising an amino acid sequence having at least 50% amino acid identity to the amino acid sequence of Table 5 (SEQ ID NO: 7), preferably at least 60%, more preferably at least 70% or at least 80% and most preferably at least 90% to SEQ ID NO: 7.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) J. Mol. Biol. 215: 403-10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman The invention further provides peptide fragments and fusion proteins of the proteins disclosed herein.

The invention further provides a method for producing the proteins encoded by the Ulimyc, Corniculmyc or Japmyc genes, comprising culturing host cells to permit expression of a Ulimyc, Corniculmyc or Japmyc protein-encoding polynucleotide and production of the protein.

The proteins and peptide fragments and fusion proteins have utility, as described herein, for the preparation of polyclonal and monoclonal antibodies to Ulimyc, Corniculmyc or Japmyc peptides, for the identification of binding partners or interactive partners of the Ulimyc, Corniculmyc or Japmyc. For uses of the protein, the present invention provides substantially pure peptides or derivatives of such peptides which comprise portions of the Ulimyc, Corniculmyc or Japmyc amino acid sequence disclosed or enabled herein and which may vary from as little as about 1 or 2 amino acids (e.g. for use as immunogens) to the complete amino acid sequence of the peptides. The invention provides substantially pure peptides comprising sequences corresponding to at least 5 consecutive amino acids of the Ulimyc, Corniculmyc or Japmyc protein disclosed or enabled herein.

The proteins and peptides of the invention may be used as a basis for the identification of other tannin regulatory genes, for example, using yeast two-hybrid screening.

The peptides of the invention may be isolated and purified by any conventional method suitable in relation to the properties revealed by the amino acid sequences of these peptides and proteins.

Alternatively, cell lines may be produced which overexpress the Ulimyc, Corniculmyc or Japmyc gene product, allowing purification of the protein and cleaved peptides for biochemical characterization, large-scale production, antibody production or for use in assays.

For protein expression, eukaryotic and prokaryotic expression systems may be generated in which the Ulimyc, Corniculmyc or Japmyc gene sequence is introduced into a plasmid or other vector which is then introduced into living cells. Constructs in which the Ulimyc, Corniculmyc or Japmyc cDNA sequence containing the entire open reading frame is inserted in the correct orientation into an expression plasmid may be used for protein expression. Alternatively, portions of the sequence may be inserted. Prokaryotic and eukaryotic expression systems allow various important functional domains of the protein to be recovered as fusion proteins and used for binding, structural and functional studies and also for the generation of appropriate antibodies.

Typical expression vectors contain promoters that direct the synthesis of large amounts of mRNA corresponding to the gene. They may also include sequences allowing autonomous replication within the host organism, sequences that encode genetic traits that allow cells containing the vectors to be selected, and sequences that increase the efficiency with which the mRNA is translated. Stable long-term vectors may be maintained as freely replicating entities by using regulatory elements of viruses. Cell lines may also be produced which have integrated the vector into the genomic DNA and in this manner the gene product is produced on a continuous basis.

In a further embodiment of the present invention is the isolated Ulimyc, Corniculmyc or Japmyc nucleotide sequence, controlled by a suitable promoter, for use in regulation of condensed tannin content in plant cells and tissues.

As used herein, a suitable promoter may be for example but not limited to a 35S promoter, a nos promoter, small subunit rubisco promoter, light-induced promoters, leaf specific promoters or any other promoters which are expressed in the desired tissue in accordance with the selected application. Plant cells and tissues include but are not limited to leaf, stem, flower, root, developing seed, mature seed and seedling.

In accordance with a further embodiment, the invention provides a transgenic plant or plant cell transformed with a nucleic acid comprising a nucleotide sequence encoding the amino acid sequence of SEQ ID NO: 4, SEQ ID NO:5, SEQ ID NO:6, SEQ ID NO:7, SEQ ID NO:9 or SEQ ID NO: 10 and wherein the nucleotide sequence is expressed.

In a preferred embodiment, the plant or plant cell is transformed with and expresses a nucleic acid comprising the nucleotide sequence of SEQ ID NO: 1, SEQ ID NO: 2, SEQ ID NO: 3 or SEQ ID NO: 8.

The plant or plant cell may be a monocot or a dicot. For example, the plant or plant cell may be selected from the group consisting of a legume, for example alfalfa and white clover, a cereal, for example barley, or a crucifer, for example *Brassica napus*.

The invention further provides a method for inducing or increasing condensed tannin synthesis in a plant comprising:

(a) transforming a plant with an isolated nucleic acid of claim 1; or with an isolated nucleic acid encoding any one of the amino acid sequences of Table 4 (SEQ ID NO: 4, 5, 6), Table 5 (SEQ ID NO: 7) or Table 7 (SEQ ID NO: 9, 10); and (b) selecting a transformed plant wherein the nucleic acid is expressed, whereby condensed tannin synthesis is increased or decreased in the plant.

This method may be used to increase or induce condensed tannin synthesis in a wide variety of plants, including legumes, for example sainfoin, peans and lentils, alfalfa, cereals, for example barley, or crucifers, for example *Brassica napus*.

The invention further provides a method for suppressing or reducing condensed tannin synthesis in a plant comprising:

(a) transforming a plant with an isolated nucleic acid comprising the antisense strand of any of the nucleotide sequences of the present invention (SEQ ID NOs: 4-7, 9 or 10).

The method may be used to suppress or reduce condensed tannin synthesis in a variety of plants, including legumes, for example sainfoin, cereals, for example barley, or crucifers, for example *Brassica napus*.

In one preferred aspect, condensed tannin synthesis is suppressed or reduced by transforming a desired plant cell, tissue or entire plant with a nucleic acid sequence of Table 3 (SEQ ID NO:3).

In accordance with an embodiment of the invention, is the use of the Ulimyc, Corniculmyc or Japmyc gene sequence or protein product to regulate the production/expression of flavonoids of the phenylpropanoid/flavonoid pathway in plants and plant tissues and/or to regulate condensed tannin synthesis.

According to a further embodiment of the invention is the use of the Ulimyc or Corniculmyc gene in a plant cell or tissue, to increase condensed tannin content for improving forage quality and as a result, improving animal health, carcass weight gain, milk and wool production and decreasing bloat in animals and reducing silage spoilage. Such plants include but are not limited to alfalfa (lucerne; *Medicago sativa* and *M. falcata* and hybrids between them), white clover (*Trifolium repens*), red clover (*T. pratense*), alsike clover (*T. hybridum*), sweetclover (*Melilotus alba* and *M. officinalis*) and subterrain clover (*P. subterranium*).

Depending on the specific application, condensed tannin levels may be increased or decreased in a variety of plants which include but are not limited to alfalfa, white clover (*Trifolium repens*), red clover (*T. pratense*), alsike clover (*T. hybridum*), sweetclover (*Melilotus alba* and *M. officinalis*), sainfoin (*Onobrychis viciifolia*), big trefoil (*Lotus uliginosis*), birdsfoot trefoil (*L. corniculatus*), cicer milkvetch (*Astragalus cicer*), sericea (*Lespedeza cuneata*), Kobe lespedeza (*Kummerowia striata*), Korean lespedeza (*K. stiputlacea*), trees, shrubs and herbacious plants in general.

According to another aspect of the invention is the use of the Ulimyc, Corniculmyc or Japmyc nucleotide sequence for use in regulation of condensed tannin content in barley seed coat, specifically the testa layer, to raise the condensed tannin content of seed coat and thereby increase resistance to pathogens and pests. In this aspect, the Ulimyc, Corniculmyc or Japmyc nucleotide sequence may be expressed utilizing a seed-coat-expressed promoter in a sense orientation.

According to another aspect of the invention is the use of the Ulimyc, Corniculmyc or Japmyc nucleotide sequence for use in regulation of condensed tannin content in barley seed coat, specifically the testa layer, to lower the condensed tannin content of seed coat. In this aspect, the Ulimyc or Corniculmyc nucleotide sequence is used in an antisense direction to inhibit or downregulate the gene and subsequently cause the reduction of condensed tannins in the testa layer of the barley seed coat.

In accordance with another aspect of the present invention is a method for altering the condensed tannin level in a plant or plant cell comprising transforming or treating the selected plant or plant cell with a substance selected from the group consisting of:

(a) Ulimyc, Corniculmyc or Japmyc antagonist;
(b) an antibody which binds specifically to the Ulimyc, Corniculmyc or Japmyc protein;
(c) an antisense strand comprising a nucleic acid sequence complementary to the sequence or fragment of the sequence and capable of hybridising to the nucleic acid sequence encoding the Ulimyc or Corniculmyc protein; and
(d) an agent which down regulates the expression of the Ulimyc or Corniculmyc gene.

According to another embodiment of the invention is the use of the Ulimyc or Corniculmyc gene in a plant cell or tissue, for increasing condensed tannin levels in said plant cell or tissue and thus increasing tolerance or resistance to insects and diseases.

In accordance with still a further aspect of the present invention is the use of the Ulimyc or Corniculmyc nucleotide sequence under control of a seed-coat-expressed promoter in an antisense orientation, for the purpose of reducing seed coat condensed tannin to reduce hazing in beer and fruit juice.

In accordance with a further aspect of the present invention is the use of a genetic construct comprising the Ulimyc, Corniculmyc or Japmyc nucleotide sequence in a sense or antisense orientation under the control of a suitable promoter which is capable of expression in a designated plant part for transformation of barley, alfalfa, canola or other suitable plant, for increasing tolerance or resistance to infection by fungi, viruses and/or bacteria.

In accordance with still a further aspect of the present invention is the use of a genetic construct comprising the Ulimyc, Corniculmyc or Japmyc nucleotide sequence in a sense or antisense orientation under the control of a suitable promoter for transformation into a plant cell or tissue for increasing tolerance or resistance to disease, insects, nematodes, and other pest species. In this aspect, the transformation of barley and canola is most preferred.

In accordance with still a further aspect of the present invention is the use of the Ulimyc, Corniculmyc or Japmyc nucleotide sequence for reducing condensed tannin content of seed coat in lentils (*Lens culinaris*), chickpeas (*Cicer arietinum*), soybean (*Glycine max*), beans (*Vicia* and *Phaseolus* species), grasspea (*Lathyris sativus*) and peas (*Pisum* species). In this aspect, the Ulimyc or Corniculmyc nucleotide sequence may be used in an antisense orientation under the control of a promoter which causes expression in seed coat to reduce the bitterness of seed coat which may affect palatability of these grain legumes for human food and also reduce palatability and digestibility for monogastric livestock such as pigs and chickens.

In accordance with yet still a further embodiment of the invention is the use of the Ulimyc, Corniculmyc or Japmyc nucleotide sequence for decreasing condensed tannin content of seed coat of *Brassica napus, B. rapa, B. juncea, Sinapis alba*, and other related species which can be intercrossed with these by natural means or in vitro. In this aspect, the Ulimyc or Corniculmyc nucleotide sequence is placed under the control of a suitable seed-coat-expressed promoter in the antisense orientation The resultant decreased expression of condensed tannin can decrease the fibre content of the meal fraction and increases the value of the meal fraction as feed for monogastric livestock by increasing its palatability and digestibility. This is also advantageous for feeding of laying hens in order to reduce egg taint.

According to yet another aspect of the invention is the use of the Ulimyc, Corniculmyc or Japmyc nucleotide sequence in any selected plant species, in sense or antisense orientation, to affect condensed tannin content for nutraceutical use.

According to yet another aspect of the invention is the use of the Ulimyc, Corniculmyc or Japmyc nucleotide sequence in any selected plant species, in sense or antisense orientation, to affect condensed tannin content for the purposes of altering flavour, colour and/or astringency in plants used directly or processed for food.

According to yet a further embodiment of the invention is the use of the Ulimyc, Corniculmyc or Japmyc nucleotide sequence in any selected plant species to generate plants which can then be used in land reclamation projects in order to clean up land contaminated with heavy metals. Condensed tannins are known to bind heavy metals and therefore transgenic plants producing large amounts of condensed tannins can be planted in polluted land containing heavy metals in order to chelate such metals from the earth.

BRIEF DESCRIPTION OF THE DRAWINGS

The present invention will be further understood from the following description with reference to the Figures, in which:

FIG. 1 is a diagram showing the phenylpropanoid/flavonoid pathway illustrating the formation of condensed tannins;

FIG. 2 is a Northern blot showing expression of myc factors in young leaf tissue of several forage legume species, probed with a control probe, actin (upper panel) or with a portion of Japmyc (lower panel).

FIG. 5 shows the interruption of *L. japonicus* myc gene in tan mutants which produce condensed tannins in leaves, unlike the wild type; suggesting that an inhibitor has been disrupted. *L. japonicus* variety Gifu was mutagenized with a transposon carried on T-DNA. Panel A. Southern blot of EcoR1 digests of genomic DNA from mutant and wild type *L. japonicus* and other *Lotus* species probed with *L. uliginosus* myc, showing altered size of labelled EcoR1 fragment (arrows). Tan-2 DNA was not fully digested. DNA from tan-1 hemizygous parent and wild type 3 was degraded and the load in the gel lanes was low. Panel B shows a linear map of myc gene showing positions of primers used to analyse tan mutants. Panels C & D show PCR products generated by primer pairs outlined in panel B. Panel C shows primers myc14 and myc 15; Panel D shows primers myc16 and myc17. The presence of PCR products in wild type *L. japonicus* and some mutants, together with absence of PCR products in tan-1 and tan-3 mutants (arrows) suggests interruption of the gene either by T-DNA or by the 4.8 kb tranposon pSLJ2572 (tan-1) or pSLJ3621 (tan-3) in these mutants. Panels E, F & G show *L. japonicus* young leaf incubated with butanol-HCl, which hydrolyzes condensed tannins to a deep red/black. Panel D shows closeup of wild type leaf with no condensed tannin; Panel E shows tan-1 leaf with substantial accumulation of condensed tannin and Panel F shows a closeup of Panel E.

Figure 3A:
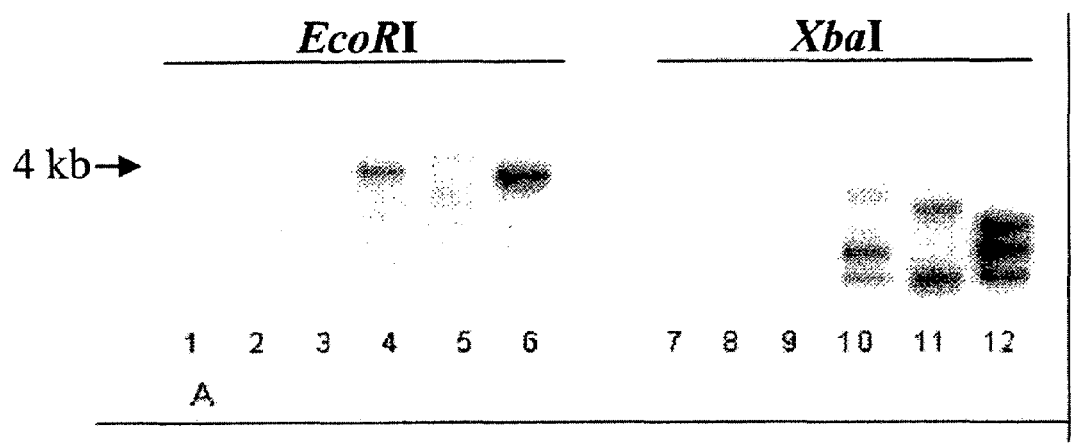
FIG. 3 shows Southern and Northern blot analysis for the *Lotus uliginosis* myc gene in tannin-containing legumes. Panel A shown a Southern blot of genomic DNA digested with EcoRI or XbaI. Lanes 1 and 7, alfalfa cv Beaver clone 1; lanes 2 and 8, alfalfa cv Beaver clone 3; lanes 3 and 9, sainfoin, lanes 4 and 10, *L. corniculatus* high tannin selection; lanes 5 and 11, *L. uliginosis* high tannin selection; lanes 6 and 12, *L. japonicus*. Panel B shows a Northern blot. Lanes 1 and 7, alfalfa cv Beaver clone 3; lane 2, sainfoin; lanes 3 and 8, *L. corniculatus* high tannin selection; lanes 4 and 9, *L. japonicus*; lanes 5 and 6, *L. uliginosis* high tannin selection. Panel C shows the relative expression of *L. uliginosis* myc gene in young legume leaves and young flowers. The data was based on the Northern blot in panel B probed with a full-length *L. uliginosis* myc probe. Hybridization band intensity was compared by densitometry and expressed relative to the staining intensity of the combined 18S and 23S rRNA bands on the gel (CT, condensed tannin accumulation).

In the drawings, preferred embodiments of the invention are illustrated by way of example. It is to be expressly understood that the description and drawings are for the purpose of illustration and as an aid to understanding, and are not intended as a definition of the limits of the invention.

DETAILED DESCRIPTION OF THE INVENTION

The present invention provides novel tannin regulatory genes that may be used to increase or decrease condensed tannin levels in plants and plant tissues. The genes were isolated and characterized from *Lotus uliginosis* (big trefoil), *Lotus japonicus* and *Lotus corniculatus* (birdsfoot trefoil) and are designated herein as Ulimyc, Japmyc and Corniculmyc respectively. The partial genomic DNA sequence of the Ulimyc gene is shown in Table 1 (Sequence ID No: 1). Its encoded amino acid sequence (Sequence ID No: 7) is shown in Table 5. The complete Ulimyc cDNA sequence is shown in Table 2 (Sequence ID No:2). The substantially entire genomic DNA sequence of the Japmyc gene is shown in Table 3 (Sequence ID No: 3) and its encoded amino acid sequence (Sequence ID No: 4, 5 and 6) is shown in Table 4. The partial genomic DNA sequence of Corniculmyc is shown in Table 6 (Sequence ID No: 8) and portions of the encoded amino acid sequence (Sequence ID No: 9 and 10) is shown in Table 7.

*L. uliginosis* is a forage legume which accumulates large amounts of condensed tannins in most tissues, especially in leaves. The isolated Ulimyc nucleic acid sequence appears to encode a novel gene of the basic helix-loop-helix (bHLH) myc-like class of regulatory proteins. For example, an alignment between the 5' end of Ulimyc and a similar region of the anthocyanin regulatory gene, delila, from *Antirrhinum majus* indicates 64% amino acid sequence homology within a 116 amino acid portion encoding the bHLH (Table 8). The genomic sequences from the homologues were aligned and compared with the Ulimyc cDNA by the clustal method to deduce the fragments of amino acid sequence illustrated in Tables 4, 5, 7 and 8. An alignment of deduced amino acids indicates >90% similarity between the three homologues (Tables 8, 9 and 10).

Figure 3B:
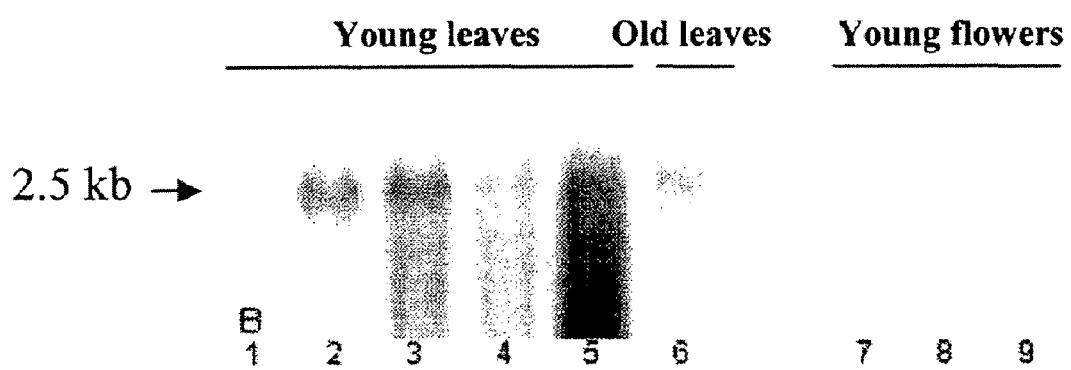
Figure 3C:
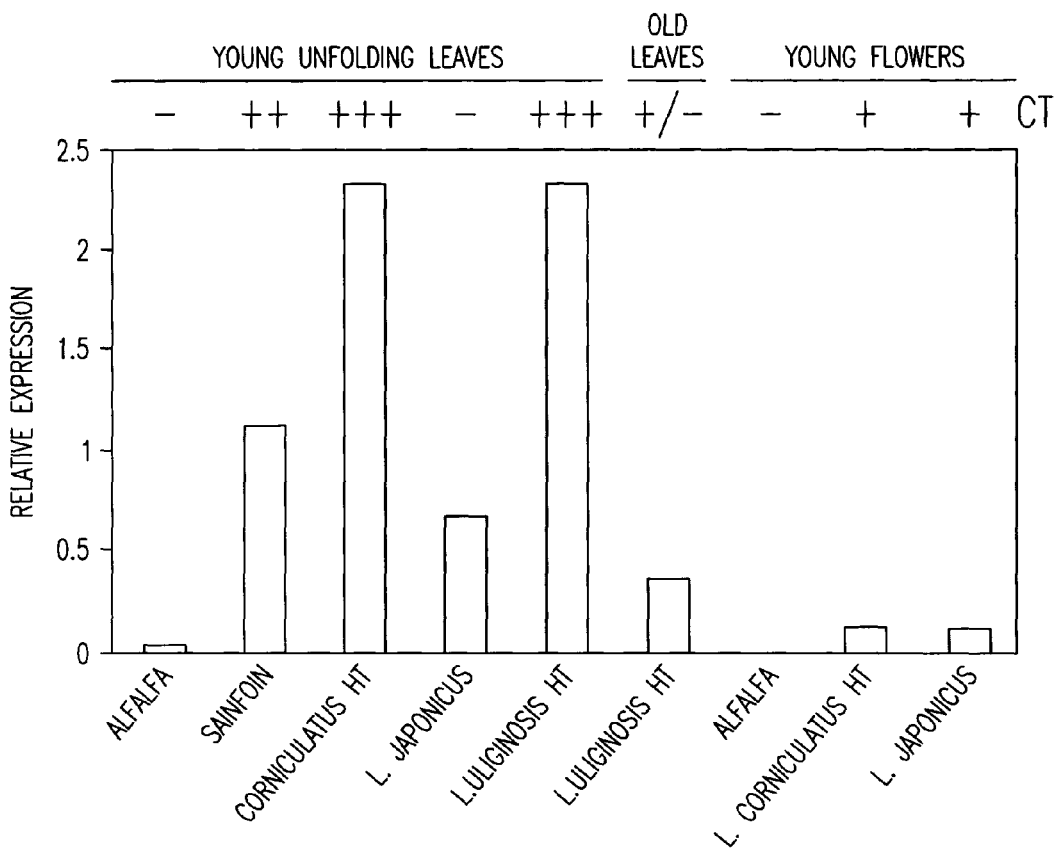

Southern blot analysis suggests that there is only one copy of the myc gene found in the three *Lotus* species tested, and that there is likely no homologous gene in alfalfa (FIG. 3, panel A, moderate to stringent hybridization conditions). Alfalfa is a legume species which does not accumulate condensed tannins in any tissue except the seed coat. However, a homologue can be detected under similar conditions in sainfoin, another forage legume that accumulates large amounts of condensed tannin in most tissues, especially in leaves.

Figure 4:
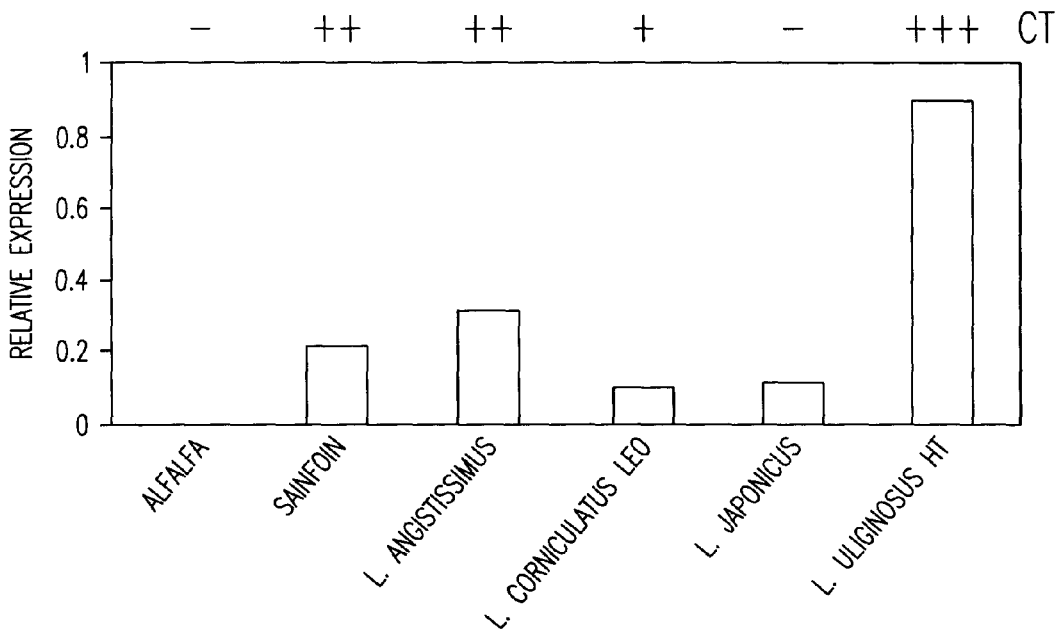
FIG. 4 shows the relative expression of the *L. uliginosis* myc gene in young legume leaves. Data is based on the Northern blot in FIG. 2 probed with the *L. japonicus* myc fragment. Hybridization band intensity was expressed relative to the intensity of actin from *Brassica napus* (CT, condensed tannin accumulation).

Gene expression studies indicate that transcripts of the *Lotus myc* gene accumulated strongly in legume tissues which accumulated moderate-to-large amounts of condensed tannins, such as in young leaves of *L. uliginosus* HT, *L. corniculatus* HT, and sainfoin (FIGS. 2, 3B, 3C, and 4). In sainfoin, it is likely that the accumulation is actually higher than indicated in FIGS. 2-3, since the Southern hybridization signal for the sainfoin orthologue is much weaker than the signal for the *Lotus* species and the Northern hybridization signal for sainfoin is strong. In comparison, transcript accumulation for the *Lotus myc* gene was low in tissues which accumulate lower amounts of condensed tannins. These tissues include senescing leaves of *L. uliginosus*, young leaves of *L. corniculatus* cv Leo, young leaves of *L. angistissimus*, *L. japonicus* and young flowers of *L. corniculatus* HT and *L. japonicus* (FIG. 3, panel B and C and FIG. 4). Finally, transcripts are not detected at all in alfalfa leaves and flowers (FIG. 3 and 4). The absent and low, hybridization signals of young alfalfa and senescing *L. uliginosis* leaves, respectively, were obtained even with a 2- to 3-fold higher amount of RNA on the Northern blot compared with the young *Lotus* leaf samples.

Curiously, transcripts for the *Lotus myc* gene were detected in low-to-moderate abundance in young leaves of *Lotus japonicus*, a legume species which does not normally accumulate condensed tannins in leaves (FIGS. 2, 3B, 3C, and 4). At the same time, a naturally-induced mutant and several T-DNA/Tn insertion "tan" mutants had been recovered earlier from *Lotus japonicus* which the leaves strongly accumulated condensed tannins (FIG. 5, panel E and F) (Gruber et al., 1999, 2000, Skadhauge, 1996). Consequently, some of the tan mutants of *L. japonicus* were analyzed to determine the relationship of these mutations to the *Lotus myc* gene.

Southern blot analysis illustrates the myc gene in unmutated *L. japonicus* is actually disrupted in several of the mutant lines, i.e. tan-1 and tan-3 have additional EcoR1 restriction fragments (FIG. 5, panel A). When either of two sets of primer pairs encompassing the region were used to amplify genomic DNA from the mutant lines (myc14/15 or myc16/17, Table 11, FIG. 5, panel B), the typical PCR product of the unmutated line was also absent in tan-1 and tan-3

(FIG. 5, panels C and D). This indicates that disruption of the myc gene in these two mutants has occurred within the region specified by the overlap (~410 bp in the cDNA, ~800 bp in the genomic DNA). Whether the mutation resulted from the initial insertion of T-DNA, from transposition of the transposase, or from recombination arising from either event was not determined. However, an insertion into this region would make the region between primers too large to amplify under the conditions used.

Together, the data shown in FIG. 5 indicates that the Japmyc gene in Lotus japonicus is actually an inhibitor of leaf condensed tannins in spite of its strong sequence similarity to Ulimyc and Cornimyc, since disruption of the gene is correlated with accumulation of condensed tannin expression in the mutants. This finding explains the fact that myc transcripts accumulate in L. japonicus leaves in low-to-moderate abundance. A parallel situation can be found in which the C1-I gene which inhibits anthocyanin accumulation in maize is highly similar in sequence to C1, a myb gene which stimulates anthocyanin production (Goff et al., 1991).

An alignment of Ulimyc with the most closely related myc-like genes indicates 36-41% identity over the full length amino acid sequence with G. hirsutum myc, the most similar dicot gene (Table 11, GenBank Accession number AAK19613). Ulimyc also has 30-34% identity to maize B-Peru (the most similar monocot gene, GenBank Accession number A41388) and 27-29% identity to Lc, a B-Peru homologue (Table 10). All three of these orthologues stimulate anthocyanin accumulation in their native species. Lc and B-Peru and the delila gene from Antirrhinum majus have also been shown to stimulate anthocyanin induction in a number of other plant species, including tomato, tobacco, wheat, oats, barley and white clover (Mooney et al., 1995; Wang et al., 1991; Bradley et al., 1998; De Majnik et al., 1998). The example indicates the uniqueness of the Lotus myc gene sequences compared with anthocyanin-regulatory genes from other species.

The idenfication of the novel regulatory genes and proteins encoded therefrom allow the use of these genes and proteins in order to alter the phenylpropanoid/flavonoid pathway in various plant cells and tissues where genes of this pathway are expressed. The L. uliginosus and L. corniculatus nucleic acids of the present invention have use in the induction of the flavonoid pathway, especially the branch of the pathway specific to condensed tannin accumulation; and therefore its introduction into other plant species under a suitable promoter will induce condensed tannin production, for example, to improve forage quality for grazing ruminant animals.

The L. japonicus nucleic acids of the present invention, as well as antisense constructs of the L. uliginosus and L. corniculatus forms, will be useful for the prevention of condensed tannin accumulation in species where reduction of condensed tannin would improve utility and quality for a specific purpose, for example, to reduce tannins in hulls of peas, lentils and rapeseed to improve palatability and digestibility for consumption by humans, fish or monogastric animals.

From the method of isolation using PCR, and gene expression and disruption patterns, it appears that these genes are regulatory genes responsible for the transcription and expression of several of the flavonoid genes indicated in FIG. 1. The knowledge of the Ulimyc, Japmyc and Corniculmyc gene sequence allows the modulation of tannin levels in plants where and, as a result, provide various different uses of such genes and proteins in the agriculture and food industries.

The identification of the Ulimyc, Japmyc and Corniculmyc genes provides for the use of these genes as well as portions of the genes, allelic variants, homologues or antisense inhibitory nucleic acid sequences in various plants and plant tissues in order to alter condensed tannin levels. A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque Plant Sci. (Limerick) 105:125-149 (1995); Pantopoulos In Progress in Nucleic Acid Research and Molecular Biology, Vol. 48. Cohn, W. E. and K. Moldave (Ed.). Academic Press, Inc.: San Diego, Calif, USA; London, England, UK. p. 181-238; Heiser et al. Plant Sci. (Shannon) 127:61-69 (1997)) and by preventing the accumulation of MRNA which encodes the protein of interest, (see, Baulcombe Plant Mol. Bio. 32:79-88 (1996); Prins and Goldbach Arch. Virol. 141:2259-2276 (1996); Metzlaff et al. Cell 88:845-854 (1997), Sheehy et al., Proc. Nat. Acad. Sci. USA, 85:8805-8809 (1988), and Hiatt et al., U.S. Pat. No. 4,801,340).

The present invention also encompasses the expression product of any of the nucleic acid sequences disclosed and methods of making the expression product by expression from encoding nucleic acid therefore under suitable conditions, which may be in suitable host cells. Following expression, the product may be isolated from the expression system and may be used as desired, for instance in formulation of a composition including at least one additional component Purified proteins or a fragment, mutant, derivative or variant thereof of the present invention, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80-82). Antibodies may be polygonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide encoded by any one of the SEQ ID Nos: 1, 2, 3 or 8 (in accordance with embodiments disclosed herein), comprising screening candidate polypeptides with a polypeptide comprising the antigen-binding domain of an antibody (for example whole antibody or a fragment thereof) which is able to bind a polypeptide or fragment, variant or derivative thereof of the present invention or preferably has binding specificity for such a polypeptide.

Candidate polypeptides for screening may for instance be the products of an expression library created using nucleic acid derived from a plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases.

The invention can be used in any plant type which expresses any of the genes of the phenylpropanoid/flavonoid pathway. With respect to antisense constructs, these inhibitory sequences inhibit the expression of the gene leading to decreased levels of condensed tannins. Such inhibitory antisense constructs must be at least partially complementary to the nucleic acid gene sequences of the present invention and will usually be from at least 10-20 nucleotides in length, more typically about 30 nucleotides in length, more usually 50 nucleotides in length and most preferably at least 100 nucleotides in length. It is understood by those skilled in the art that inhibitory nucleotide sequences can be designed in order to bind and inhibit messenger RNA or alternatively, to block gene transcription by binding to one strand of the gene during transcription. In this case, the transcript may have either sense or antisense orientation with respect to the target gene sequence and can target any sequence of the gene.

The novel genes can be used in genetic constructs in order to transform a selected plant, plant tissue or plant cell using suitable transformation techniques, a number of which are well known to those skilled in the art of plant molecular biology. By plant transformation is meant the introduction of an external nucleic acid sequence into the plant genome. Transformation techniques include calcium phosphate transfection, DEAE-dextran transfection, electroporation, microinjection, protoplast fusion and liposome-mediated transfection. Alternatively, a plant virus such as CaMV may be used as a vector for introducing foreign nucleic acid into plant cells or a high velocity ballistic penetration using small particles (Klein et al., 1987).

A most preferred method for introducing nucleic acid segments into plant cells is to infect a plant cell or plant tissue with *Agrobacterium tumefaciens* which has been transformed with the nucleic acid segment (Horsch et al., 1984). Plants transformed with the nucleic acid sequences of the present invention may be produced by standard techniques which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-8721 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) Plant Tissue and Cell Culture, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. Plant Cell Physiol. 29: 1353 (1984)), or the vortexing method (e.g. Kindle, PNAS U.S.A. 87: 1228 (1990d) Physical methods for the transformation of plant cells are reviewed in Oard, 1991, Biotech. Adv. 9: 1-11.

Microprojectile bombardment, electroporation and direct DNA uptake are preferred where *Agrobacterium* is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., Cell Culture and Somatic Cell Genetics of Plants, Vol I, II and III, Laboratory Procedures and Their Applications, Academic Press, 1984, and Weissbach and Weissbach, Methods for Plant Molecular Biology, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

In order to produce Ulimyc or Japmyc proteins, the genes disclosed herein may also be used to transform host cells suitable for recombinant production of the gene products. Such host cells may be selected from the group consisting of *E. coli, Pseudomonas, Bacillus subtilis*, or other *bacilli*, other bacteria, yeast, fungi, insect (using baculoviral vectors for expression), or plant cells. Methods for producing appropriate vectors, for transforming cells with those vectors and for identifying transformants are described in the scientific literature, as for example, but not limited to, Sambrook et al. (1989), *Molecular Cloning: A Laboratory Manual*, Cold Spring Harbor Laboratory Press, Cold Spring Harbor, N.Y. and more importantly in Glick, B. R. and Thompson, J. E. 1993, *Methods in Plant Molecular Biology and Biotechnology*, CRC Press, Boca Raton.

The cellular distribution of the Ulimyc or Japmyc gene product in tissues can be analyzed by reverse transcriptase PCR analysis or by Northern blot analysis. Antibodies to the gene product can also be generated for several applications including both immunocytochemical and immunofluorescence techniques to visualize the proteins directly in cells and tissues in order to establish the cellular location of the protein.

Use of Ulimyc, Corniculmyc or Japmyc to Alter Plant Tannin Levels for the Improvement of Forage Quality The Ulimyc, Corniculmyc or Japmyc gene sequences or homologues thereof, may be used to transform legume forage plants to increase their quality by increasing tannin levels, for example in alfalfa (lucerne, *Medicago sativa* and *M. falcate*) or in other such highly-nutritious protein-rich forage/feed for ruminants, such as sweetclover, red clover, white clover, alsike clover, or subterrain clover, providing strong economic benefits to the beef, dairy, and sheep industries. In the case of Japmyc, this gene can be suppressed in order to increase condensed tannin levels. First, tannins eliminate the close-celled, protein-stabilized foam, which forms in the rumen and causes bloat (Howarth et al., 1991; Lees, 1992; Tanner et al., 1995; Coulman, 1999). This foam presses outward and may press so strongly on the diaphragm that the animal suffocates and dies. In milder forms, bloat causes cattle to go off their feed and gain weight more slowly. Bloat is the major constraint to raising and maintaining cattle and sheep on pasture with >50% alfalfa or white clover.

Second, an excessive initial rate of digestion occurs in the rumen with soft-leafed legumes such as alfalfa and white clover, resulting in a significant loss of protein to urea and ammonia (15-25% for alfalfa). Condensed tannins "capture" this protein (called protein bypass or ruminal escape protein) by lowering the initial rate of digestion and improving peptide and amino acid flow to the small intestine (Tanner et al., 1994; Waghorn et al., 1997; McNabb et al., 1993). Hence, tannins in forage legumes should significantly improve the efficiency of conversion of alfalfa and white clover protein to ruminant meat protein, milk and wool (Min et al., 1998). Similar improvements in milk yield have been seen in dairy production in the USA with protein bypass.

Third, condensed tannins will reduce the activity of bacteria and fungi which can spoil high protein legume silage such as alfalfa and white clover.

Fourth, the capture of a greater proportion of alfalfa and white clover protein into meat, milk and wool will result in reduced ammonia smell and methane/$CO_2$ production (greenhouse gas pollution) arising from high-intensity beef and dairy operations (Waghorn, 1997).

Fifth, condensed tannins in forage and feed will improve overall ruminant health. For example, cattle and sheep feeding on mixtures which include tannins show a reduced parasite load in their intestines compared with mixtures without tannin (Neizen et al., 1995; Waghom et al., 1997).

Studies at the Brandon Research Station (Agriculture and Agri-Food Canada) indicate that approximately 60% of beef steers and 100% of heifers can be finished off inexpensively if grazed directly on 100% alfalfa pasture, compared with the usual but costly 90-day grain-fed stay in a feedlot, as long as the herd was carefully managed to prevent bloat. The remainder could be finished with about 30-60 feedlot days. Dramatically lowered costs can be obtained even when cattle are raised in mixed pastures which include alfalfa. For example, a month of grazing on a 50% sainfoin-50% alfalfa irrigated pasture (where sainfoin forage contains 3-8% fresh weight in condensed tannins) yielded weight gains in cattle comparable to those achieved in a feedlot, and without any bloat.

Improvements to alfalfa forage quality using condensed tannins can be made without compromising high nutritional index and total digestibility, particularly for alfalfa Forage legumes such as sainfoin (*Oazobrychis viciifolia*) and birdsfoot trefoil (*Lotus corniculatus*) do not cause bloat in ruminants. This has been connected to the presence of condensed tannins in their leaves. These plant species display a total nutritional digestibility and in vitro gas production which is similar to that produced by alfalfa at comparable growth stages (Fay et al., 1980). The variation in response by ruminant microorganisms when exposed to condensed tannin may be at the root of the improvement noted when tannin-containing plant species are fed to ruminants (Bae et al., 1993a; 1993b; Jones et al., 1994). Other methods of bloat control by cultivating mixed species pastures and by adding purified tannin as a prophylactic into the drinking water are projected to be less cost-effective or more management-intensive than a tannin-containing variety of alfalfa.

In accordance with a further aspect of the invention, one can also reduce the tannin content of plants, for example by suppressing expression of the Ulimyc or Corniculmyc genes or overexpress the Japmyc gene.

Some plant species have such high leaf condensed tannin content that they become unpalatable to livestock and some wildlife. Examples include browse species in the tropics (Mangan, 1988; Furstenburg, 1994) and cicer milkvetch (*Astragalus cicer*). The invention permits the manipulation of the tannin content of such species.

Use of Ulimyc, Corniculmyc or Japmyc for Producing Optimal Condensed Tannin Levels for Ruminant Forage The development of high quality forage depends not only on the induction of genes to enable tannin biochemistry to function, but also on the optimization of tannin content in relation to the plant source. The Ulimyc, Corniculmyc or Japmyc tannin regulatory genes can be used to regulate the content of condensed tannin, opening the possibility to tailor tannin content for specific forage species. One research group recently estimated that 0.5% DM tannin would give complete bloat-safety (Li et al., 1996). Another group predicted a 10-15% increase in meat, milk and wool production, if 2-3% DM tannin was present in the animal diet (McNabb et al., 1993). Studies indicate that major rumen fibre-digesting and protein-digesting bacteria and fungi can tolerate as much as 200 μg/ml of tannin with no loss of viability and with no change in normal digestion rates (Bae et al., 1993a and b; Jones et al., 1994). This dose is well within the range for bloat-safety. Higher doses of tannin did cause problems in digestion in these latter studies, and the maximum acceptable tannin dose varied with the plant source. In these latter studies, purified sainfoin tannins caused the fewest difficulties to rumen bacterial digestion profiles. However, the source of the tannins proved unimportant for ruminal foam reduction in vitro (Tanner et al., 1995).

Use of Ulimyc, Corniculmyc or Japmyc to Reduce Tannin Levels to Reduce Protein Haze in Beer and Juice Barley contains condensed tannin in the testa layer of the seed coat. The condensed tannins are released during processing of malting barley and cause a haze of precipitated protein to form slowly in beer during cold storage. Considered undesirable to the appearance of beer, these precipitates are removed by chemical filtration before bottling. Haze-free cultivars of barley lacking testa condensed tannin have been developed by chemical mutagenesis programs (Erdal, 1986; von Wettstein et al., 1979; Outtrup, 1992), but the resultant plants required considerable backcrossing and intercrossing to develop high yielding malting barley lines. The ability to reduce condensed tannin in malting barley, for example by transformation with an antisense Ulimyc or Corniculmyc gene or down regulated Japmyc gene, therefore has application for breeders in the brewing industry.

A similar approach to breeding apple lines with low tannin in the fruit and peel could reduce the unpredictable formation of chill haze in juice made from apples and other fruit and, consequently, improve the shelf-life of juice (Lees et al., 1995; Beveridge et al., 1997). The strategy could be applied to other fruit as well, since tannins are expressed in fruit of many edible fruit species. The reduction in tannin content would be balanced among the need for haze reduction, the requirement for astringency (taste) of the juice, and pathogen and insect resistance.

Use of Ulimyc, Corniculmyc or Japmyc to Alter Plant Tannin Levels as Deterrents to Insects, Fungi, Bacteria and Birds Condensed tannins are thought to be a broad spectrum defence strategy against herbivores and pathogens for many plant species. As a result, the novel Corniculmyc, Ulimyc or Japmyc genes of the present invention can be used to transform selected plant species in order to increase condensed tannin levels and as a result provide resistance or deterrence against pathogens, insects and birds.

When tested for their effect on insect pests, condensed tannin efficacy is dependent on concentration and whether the insect is able to tolerate or deactivate the condensed tannin. Insects not normally subjected to tannin diets or specialist insects are especially vulnerable. For example, condensed tannins inhibited growth of grasshoppers at high doses, but did not deter their feeding; while the crucifer flea beetle (*Phyllotreta crucifera*) and diamondback moth (*Plutella* spp.) were inhibited from feeding at lower doses (Muir et al., 1999). Other insect pests are known to be affected by condensed tannins as well.

Condensed tannins also have antifungal and antiviral properties. Scab-resistant apples have higher amounts of flavan-3-ols in leaf and fruit skins (Treutter and Feucht, 1990), and grain mould is inhibited by tannins (Jambunathan et al., 1986). The potency of condensed tannins as an antifungal agent can be dependent on the specific structure of the polymer. For example, the potency of the cocao procyanidin against *Crimpellis perniciosa* correlated with increasing polymer molecular weight (Brownlee et al., 1992). Other fungal pathogens known to be inhibited by condensed tannins include *Fusarium* (Skadhauge, 1996; Skadhauge et al., 1997; von Wettstein and Hagie, 1998). Plant viruses can also be inhibited with condensed tannins (Zhang et al., 1990).

Birds can also be deterred from feeding on crops by condensed tannins. Bird-deterring sorghum lines are rich in condensed tannins compared with lines which are susceptible (Reed et al., 1987).

Use of Ulimyc or Japmyc to Alter Tannin Levels in Seeds and Grains to Improve Seed Quality in Oilseeds and Grain Legumes Reduction of tannins in specific tissues of oilseed and grain legume species would improve their feed and food quality and industrial potential. For crops such as rapeseed (canola) and soybean, which are fractionated chiefly into oil and a protein component used for animal feed, seed coat tannins contribute to the indigestible fibre fraction and are detrimental to the total value of the crop (Simbaya et al., 1995; Marles and Gruber, unpublished). Health and digestion of poultry and swine can be negatively affected by even low quantities of dietary condensed tannins in their diets. Tannins in rapeseed feed are considered the basis for the fishy smell in tainted eggs, since tannins block metabolism of trimethylamine to an odorless compound by inhibiting TMA oxidase (Naczk and Shahidi, 1992). Mutant barley lines that are free of condensed tannins in the seeds have been developed and, when used in feed, give improved rates of weight gain in chickens (Jende-Strid, 1993; Newman et al., 1984).

For grain legume crops such as lentils (*Lens culinaris*), peas (*Pisum sativum*) and soybeans (*Glycine max*), varieties with low or no condensed tannin in the seed coat are preferred particularly for human consumption because of the bitterness of these compounds; tannin-free varieties may command a premium price. Reduction of seed coat condensed tannin in canola meal might also increase the potential of canola meal for the human food market.

While mutants and variants with low or no levels of seed coat tannin exist in several of these species, use of an antisense Ulimyc or Japmyc regulatory gene introduced by transformation allows the quick adaptation of good varieties to these higher-value uses.

Use of Ulimyc, Corniculmyc or Japmyc for Nutraceutical Applications

Condensed tannins have been shown to inhibit a variety of enzymes such as xanthine oxidase (Costantino et al., 1992) and protein kinases (Polya and Foo, 1994). Plant extracts containing condensed tannins have been used to inhibit pectinase and cellulase (Bell et al., 1962). Condensed tannins are excellent antioxidants. The measured efficiency compared with known antioxidants such as vitamin E and B-hydroxytoluene or B-hydroxyanisol is dependent on the plant source, the polymer structure, and the method of measurement (Muir, 1997). Crude extracts containing high concentrations of condensed tannins from red and black currents, red and black raspberries and highbush blueberries are all highly active at scavenging superoxide radicals (Costantino et al., 1992). The UV absorptive properties of condensed tannins lend additional potential for plants containing condensed tannins to be used in skin creams and sunprotectants. This information suggests that plants developed with a transgene which stimulated condensed tannin biosynthesis such as the Ulimyc, Corniculmyc or Japmyc gene of the present invention may have potential as health foods and nutraceuticals.

Use of Ulimyc, Corniculmyc or Japmyc to Affect Flavour, Colour and Taste of Food and Wine Condensed tannins contribute to the astringency, bitter flavours, and colour in fruit, fruit juice and red wine (Lea, 1982; Singleton, 1992). These characteristics are in proportion to their content and polymer size. For example in cider, a maximum perceived bitterness response occurred with tetrameric procyanidin, while the response for astringency continued to increase with molecular size (Lea, 1992). Since they are easily oxidizable phenolics, condensed tannins contribute to the browning that occurs when fruit spoils. Their presence coupled with chlorogenic acid makes a major contribution to the light yellow/brown colour of apple juice (Lea, 1992). In red wine, anthocyanins covalently link with condensed tannins, preventing them from precipitating with proteins (Singleton, 1992). The tannins contribute to the warmer colour tones of matured red wine (Liao et al., 1992). A gene such as Ulimyc or Japmyc which would regulate tannin content may have use in the control of these characters.

EXAMPLES

The examples are described for the purposes of illustration and are not intended to limit the scope of the invention.

Methods of synthetic chemistry, protein and peptide biochemistry and molecular biology referred to but not explicitly described in this disclosure and examples are reported in the scientific literature and are well known to those skilled in the art.

Unless otherwise detailed, molecular biology procedures were carried out following standard methods such as those described in Sambrook et al., 1989; Ausubel et al., 1999; Gelvin et al., 1998 and Griffin and Griffin, 1994.

Isolation of Genes

To isolate myc genes involved in condensed tannin regulation, plant genomic DNA from Lotus uliginosis, L. japonicus and L. corniculatus was prepared by a modified Dellaporter method or using a Quiagen plant DNA mini-columns. Primers were developed to myc regions well conserved between regulatory genes involved in anthocyanin biosynthesis, delila of Antirrhinum majus (GenBank Accession number AAK19613) and B-Peru of Zea mays (GenBank Accession number A41388) (Quattrochio et al., 1998). Primers were commercially prepared by GibcoBRL (Life Technologies), Integrated DNA Technologies, Inc., or the Plant Biotechnology Institute, National Research Council of Canada in Saskatoon. PCR was conducted at several annealing temperatures on a Perkin Elmer DNA thermal cycler Model 480 using L. japonicus and L. uliginosus genomic DNA until 350 bp fragments was detected by agarose gel electrophoresis. PCR fragments were cloned into pGEM®-T (Promega), transformed by electroporation, and selected colonies used for DNA isolation and DNA sequencing using fluorescent primers. The fragments were found to strongly resemble other myc sequences in GenBank. Gel fragments for sequencing and subcloning were purified prior using Prep-A-Gene® (Biorad).

Nested primers facing upstream and downstream were developed to isolate the remaining cDNA sequence of L. uliginosus by 3' and 5' RACE (Rapid amplification of cDNA ends) (Table 11). RNA was prepared from newly-opened leaf of greenhouse plants by the borax method (Wilkins and Smart, 1996). RACE was carried out using a GibcoBRL 5' RACE kit with additional oligo dT primer and BBT primer (GibcoBRL). The isolated fragments were cloned into pGEM-T, transformed into E. coli, purified and sequenced as previously described. Sequence data was analysed using Lasergene™ (DNA Star) and publicly available gene analysis programs. The L. uliginosus cDNA sequence data was used to develop additional primers which were subsequently used to amplify additional genomic DNA from L. japonicus and L. corniculatus.

The Lotus myc gene was analyzed using several legume species with a wide range of expression in leaf tissue, from absent to highly concentrated. For Southern blot analysis, DNA was isolated as above, digested overnight with 50 U EcoR1 or Xba1, separated on agarose gels, denatured using 0.4 M NaOH, and blotted overnight onto nylon membranes (Boeringer-Mannheim). For Northern blot analysis, RNA was prepared from newly-unfolding leaves of greenhouse plants by using a RNA preparatory column (Quiagen) for alfalfa or by the borax method for all other species, since condensed tannin interferes with RNA isolation by most methods (Wilkins and Smart, 1996). $^{32}$P-labelled DNA probes were prepared from gel-purified digested plasmid DNA fragments covering the myc-like region of L. japonicus and L. uliginosis using a standard random priming kit (GibcoBRL). Radiolabelled probe fragments were purified from unincorporated nucleotides using a S-300 column (Pharmacia). Hybridization was conducted using standard methods, followed by washing the blots to moderate or high stringency.

Analysis of the myc gene was also conducted in Lotus japonicus mutants which accumulate leaf condensed tannins (Gruber et al., 1998, 2000, Skadhauge, 1996). Southern blot analysis was conducted on EcoR1-digested DNA using nearly a nearly full-length L. uliginosus myc fragment. A size change in mutants tan-1 and tan-3 indicated sequence alterations in the immediate vicinity of the myc gene. Subsequently, PCR was conducted using primer pairs myc14+15 or myc16+17 spanning most of the myc gene (overlap between these two primer pairs is ~410 bp in cDNA sequence (~800 in genomic DNA) (Table 11). Hot-start PCR reactions, containing 0.1-2 tg DNA, 100 pM primers, MgCl$_2$, and Taq polymerase (GibcoBRL) in a standard reaction buffer (20 μl), were conducted using 30 cycles (30 sec 94°; 45 sec 52°; 2 min 72°), and a portion of the product analyzed on 20% agarose gels in TBE buffer.

Plant tissues were analyzed for condensed tannins and anthocyanins by slow Butanol:HCl hydrolysis according to Skadhauge et al. (1997), Lees et al. (1993, 1994).

It is known that modifications and variations of the present invention as set forth herein may be made without departing from the spirit and scope thereof. The specific embodiments described herein are given by way of example only and the invention is not limited thereto.

TABLE 1

Partial genomic ulimyc ggaatggagggatgggttctacaatggagacattaagacxxxxxxxxxxxxgggtgatgggttct      (Sequence ID NO:1)

acaatggagacattaagacaatgaagacagtgcaaaccatggaaactaaggctgataaaataggcctg cagaggagtgaacaactgagagaactatacaggtttcttcttgaaggtgaagctgacccacaagctaaa agaccttctgcttcattatctccagaggatctctcagattcagagtggtattacttggtttgcatgatcctttgt gttctatcccaaccaaaggtaccatatatgctcttatctcatttaattcatatagggattaattaatgatttgttt ctttgtaaatttttctagttttttttatatttaaacatgtagagttttctttttcttctcacacagtttgcctggaaaag cactagaaattggtgaaacagtgtggctatgcaatgctcagcaagcagatagtaaattttttctctcgttctttt gctagcgaaggt

TABLE 2

Complete cDNA sequence of uli myc gene from *Lotus uliginosus*.

GTGATGACTAGTACTACTCTATACACTGAAAGTAACCGAAGTGAATTTGA (Sequence ID No:2)
GCAGTGTTGTAATGCCATTTACTGTTGACTGTCTGAAAGTAAACAAGCAA
AGCTAGCAGGAGAAGAATGGCCGTTGGGAGCCCAAAGCATGAGAAGAAG
ATGCAGCAAAAGAACCTGAGTGCACAACTAGCTGTTGCTGTCAGAAGTAT
TCAATGGAGCTATGGAATTTTCTGGGCACCTTCAACTACTCAACAAAGAG
AACTGGAATGGAGGATGGGTTCTACAATGGAGACATTAAGACAATGAA
GACAGTGCAAACCATGGAAACTAAGGCTGATAAAATAGGCCTGCAGAGG
AGTGAACAACTGAGAGAACTATACAGGTTTCTTCTTGAAGGTGAAGCTGA
CCCACAAGCTAAAAGACCTTCTGCTTCATTATCTCCAGAGGATCTCTAGA
TTCAGAGTGGTATTACTTGGTTTGCATGTCCTTTGTGTTCTATCCCAACCAA
AGTTTGCCTGGAAAAGCACTAGAAATTGGTGAAACAGTGTGGCTATGCAA
TGCTCAGCAAGCAGATAGTAAATTTTTCTCTCGTTCTTTGCTAGCGAAGAG
TGCCTCTATTCAGACAGTGGTGTGTTTTCCCTATCTTGGAGGCGTCATTGA
GATAGGAACAACTGAAGTGGTATCTGAGGATCCTAATCTCATTCAACATG
TGAAGACATGCTTCTTAGAAGTCTCAAAGCCTACATGCTCTGACAAATCAT
CCTCTGCCCATGACAAACCACATGATGACAACAAATATCCAACATGCACT
AAGGGTGACCATGAGGTGTTTGACAAAATGCCCTTGGAGAACTCATGTTC
CTTTGCAGAAGAACTCAAATTTGATGAATATCCTGGCAGGGAATTACAAG
ATGATGATAACAATGAAGATTGTGACATGGATGGGTTCTCTGATGGTGGT
TATGACCATTATGAATCCATGATAGAGGGCATCAATGAGGGTGGTTCTTCT
CAAGTTCATTTTGTGAATGATGGTGGTGAAATCAATGGTGCCCCAGATTCC
TTGAGTTCTTGTGATTGTATGTCTGAGGCTTTTGAGAACCATGGTAAGAAG
GATTCTAAAAATGTAACCCAAATTCAACAAAGGGAGCTTCTAGACTGTGA
TGATCACTCAAAAAGTAGCTCTTTGGATATTGGAGCTGATGAAGATTTGTA
CTACACAAAAACTCTCTGTGCTATTCTGGGAAATTCATCAAGTTTTGCACA
AAATCTATGTGCAAGTAAATCTAGTTTTGTGAAATGGAAGAAAGGAGGAG
TTTCTGAAAGGAAGAGGCCGTGGTTGCAACAAATGATGTTAAAGAAGACT
TTGTTTGATGTCCCTTTTATGCACCTAAGTTGCTCCTCTCTCAAATTACAAA
AAGAAAATGGCAGAAAAGAATGGACTTCTAAATTGGAAAATGCTGATAAT
TTCATGGGGAATGTCTTCTCTGATAAGAAAAGAGAATCTAGAAACATTCA
GGTACTCAAATCTGTGGCTCCTTCTGCATGTGAGGTGGAGAAGATTTCAGT
TCTTGGTGGCACAATTAAATACTTGAAAAATGTTGAGGCAAGAGTGGAAG
AACTAGAATCTTACATGGACACTACAGCTACTGGAGCAAGAACCAAAGA
AAATGCCCAGATGTGCTAGAGCAGATATCAGATAACTATGGCCCCAGTAA
TATTTACATGGGAATGAAAAAACCTATGATAAACAAGAGGAAGGCTTGTG
ATATTGATAACATAGACACAGGGCTAGACATAATTGTTTCTGAAGAAGAT
AAGCCATTGGATGTGAAAGTCAACATGAAGGAGGAAGAGGTTCTGATTGA
GATGAAATGTCCTTACAGGGAATACATATTGTATGATATCATGGATGCCAT
AAACAATCTGCATATAGATGCACACACAGTTGATTCATCAACAGCTGATG TABLE 2-continued Complete cDNA sequence of uli myc gene from *Lotus uliginosus*.

GTGTTCTCACATTTAAACTTAAATCCAAGTTTCGAGGAGCAGCAACTGCGC

CAGTGCGGATGATCAAAGAAGCACTCTGGAAAGTATCTGGAAAGATTTGA

AATGCCTGATTGAGTTTCTCATGGAAGTAGTAGATTCTTCTAATTGGATCC

AAAA

TABLE 3

Genomic sequence of jap myc gene from *Lotus japonicus*.

GCGGGATTTGTGRGGTGATGGGTTCTACAATGGAGACATTAAGACAAGA      (Sequence ID No: 3)

AGACAGTGCAAACCATGGAAACTAAGGCTGATAAAATAGGCCTGCAGAG

GAGTGAACAACTGAGAGAACTATACAAGTTTCTTCTTGTAGGTGAAGCTG

ACCCACTAGCTAAAAGACCTTCTGCTTCATTATCTCCAGAGGATCTCTCAG

ATTCAGAGTGGTATTACTTGGTTTGCATGTCCTTTGTGTTCTACCCCAACC

AAAGTTTGCCTGGAAAAGCACTAGAAACTGGTGAAACAGTGTGGCTATGC

AATGCTCAGCAGGCAGATAGTAAATTTTTCTCTCGTTCTTTGCTAGCAAAG

AGTGCTTCTATTCAGACAGTGGTGTGTTTTCCCTATCTTGGATTTGTCATT

GAGATAGGAACAACTGAAGTGGTATCTGATRTGGCTATGCAAYGCTCAGC

AGGCAGATAGTAAATTTTTCTCTCGTTCTTTGCTAGCAAAGGTTGGATTTT

ATTCATAAATTTGATATTTTGGTTTTCATATTATATGATGTACGGACAATGT

AAGGTTGATGATATAATATGTGGCCAACCTTGGATTTGGCTCAGTGGGGT

AAACATCAATGGGTTTTATGATGCTCAATTTCGTCCTGTAAGCATTGAGCA

AGTTGGTCTCTANAAGAAATAAATATCTTTCGCAGTCTTTGATTGTATCNA

ATGGTGGGCAAAAAAGGTTCTTACGACTAAGATAAAAATGGNGGTTTTAG

ACAAAATTCCCATGGAGAACTCATGTTCCTTTGCAGAAGAACTCAAATTT

GATGAATATCCTGGCAGGGAGTTACAAGATGATGATAACAATGAAGATTG

TGACATGGATGGATTCTCTGATGGTGGTTGTGATCATTATGAATCCATGAT

AGAGGGCATCAACGAGGGTGGTTCTTCTCAAGTTCATTTTGTGAATGAAG

GTGGTGACATCAATGGTGCCCCAGATTCCTCTAGTTCTTGTGATTGTAGGT

CTGAGGCTTCTGAGAACCATGGTAAGAAGGATTCTAAAAATGTAATCCAA

ATTCAACAAAGGAGCTTCAAGACTGTGATGATAACTCAAAAAGTAGCTC

TTTGGATATTGGAGCTGATGAAGTTTTGTACTACACAAGAACTCTCTGTGC

TGTTCTGGGAAATTCATCAAGTTTTGCACAAAATCTATGTGCAAGTAAATC

TAGTTTTGTGAAATGGAATAAAGGAGGAGTTTCTGAAAGGAAGTGGCCGC

GGTTGCAACAAATGATGTTAAAGAAGACTTTGTTTGATGTCCCTTTTATGC

ACCTAAGTTGCTCCTCTCTCAAATTACAAAAAGAAAATGGAAGAAAAGAA

TGGACTTCTAAATTGGAAAATGCTGATAATTTCATGGGGAATGTCTTCTCT

GATAAGAAAAGAGAATCTAGAAACATTCAGGTGGGGAAGATTTCAGTTCT

TGGTGACACAATTCAATACTTGAAAAAGCTTGAGGCAAGAGTGGAAGAAC

TAGAATCTTACATGGACACTACAGCTACTGGAGCAAGAACCAGAAGAAAA

TABLE 3-continued

Genomic sequence of jap myc gene from *Lotus japonicus*.

```
TGCCCCAGATGTGCTAGAGCAGAAATCACTAATGCGGGCCCTGCAGGTC
CACCATATGGGATCATCTGCTGAAATTAATGGTATCACTCGATGAGTGATG
TGGCTGGGAAATTGCATGCTACAATGCTAATGGGCCTAATTAAATCTTAA
AATCTTTAGTTATTTCCGTATTANGGKCCCAAGTATTNAAATTTTTTACM
CCTCCATTCMCATGGNARGTTATTTTARCMATAGTGTCCTGTTCTGTTCTG
AAATTTTATTTATTTAGGAATATCAAAGTTCAATCTCAAAAAGCAGTGAAA
CATGTTAAGGAACCAGTTGTTATGTTTGTAAATTTGACAGATTTAGACTCT
TTTTAGCAATTTCTAAATGATGTCATATGTAGTAAGAAGTTAACAAAACCC
TTGAAGTTACTTTGTAAATATTGAAATATATTCATGTTAATTGCTAACTAT
GTGAAGGTGGAGAAGATTTCAGTTCTTGGTGACACAATTCAATACTTGAA
AAAGCTTGAGGCAAGAGTGGAAGAACTAGAATCTTACATGGACACTACAG
CTACTGGAGCAAGAACCAGAAGAAAATGCCCAGATGTGCAAGAGCAGAT
ATCAGATAACTATGGCCCCAGTAATATTTACATGGGAATGAAAAAATCTA
GGATAAACAAGAGGAAGGCTTGTGATATTGATGACATAGACACAGGGCTA
GACATAATTGTTTCAXXXXXXGCCACTGCGCNTGAGAAAAAACCAAATTT
TATGGAATATTATTGACATGTGATCACTTTTAATAATGTATTCCNACGTTG
TTTTTGGCTTCCCTCTACCCCATTTCCCAGGACTTGAAGAAACCATGTAAT
CAACCCTTGTCTCGATGCCTCCAAAAGTCTTCTTTGTAAGCTACATGCCTA
TAACTGCTAAAAGAATTCTTCCAAAAAGTAGCATGTTTAAGACCTTGTTCC
AAGTTATCTCAGTCAACCTGTTTTGAGGGGGCATTCTAACCATTTGTTACT
TAACCCTAGCTTGAAGGGAAGAGAAGAGCATGTTACTCATGGACTAAGAC
ATTATCAAAAAGATTTTGACCATTGAAAGTCATTTATTTAATGAGTAATT
TGAAAAATTATACTTGGAAGTTAGTTTTCTTTTCTTCAATACTTGAAAAGA
AATTTGAATTCTTAAAACTTCATTTCAGTTTCGAGGAGCAGCAACTGCGCC
AGTGCGGATGATCAAAGAAGCACTCTGGAAAGTATCTGGAAAGATTTGAA
ATGCCTGATTGAGTGTCTCATGGAAGTAGTAGATTCTTAATTGGATCCA
```

TABLE 4

Three deduced amino acid sequences from portions of the japmyc gene of *Lotus japonicus*, a model legume species.

Fragment A

DGFYNGDIKTMKTVQTMETKADKIGLQRSEQLRELYKFLLVGEADPLAKRPS (Sequence ID NO: 4)

ASLSPEDLSDSEWYYLVCMSFVFYPNQSLPGKALETGETVWLCNAQQADSKF

FSRSLLAKSASIQTVVCFPYLGGVIEIGTTEVVS

Fragment B

LENSCSFAEELKFDEYPGRELQDDDNNEDCDMDGFSDGGCDHYESMIEGINE (Sequence ID NO: 5)

GGSSQVHFVNEGGDINGAPDSSSSCDCRSEASENHGKKDSKNVIQIQQKELQD

CDDNSKSSSLDIGADEVLYYTRTLCAVLGNSSSFAQNLCASKSSFVKWNKGG

TABLE 4-continued

Three deduced amino acid sequences from portions of the japmyc gene of *Lotus japonicus*, a model legume species.

VSERKWLQQMMLKKTLFDVPFMHLSCSSLKNYKKKMEEKNGLLNWKMLIIS

WGMSSLIRKENLEXFRYSKSVAPSACEVEKISVLGDTIQYLKKLEARVEELES

YMDTTATGARTRRKCPRVQEQISDNYGPSNIYMGMKKSRINKRKACDIDDID

TGLDIIVS

Fragment C

FRGAATAPVRMIKEALWKVSGKI.                (Sequence ID NO: 6)

NB: Sequence from *Lotus japonicus* was deduced from genomic DNA aligned to the complete cDNA from *Lotus uliginosis*.

TABLE 5

Complete deduced amino acid sequence of ulimyc gene from *Lotus uliginosus* (big trefoil) cDNA.

MAVGSPKHEKKMQQKNLSAQLAVAVRSIQWSYGIFWAPSTTQQRELEWRD         (Sequence ID NO: 7)

GFYNGDIKTMKTVQTMETKADKIGLQRSEQLRELYRFLLEGEADPQAKRPSA

SLSPEDLSDSEWYYLVCMSFVFYPNQSLPGKALEIGETVWLCNAQQADSKFF

SRSLLAKSASIQTVVCFPYLGGVIEIGTTEVVSEDPNLIQHVKTCFLEVSKPTCS

DKSSSAHDKPHDDNKYPTCTKGDHEVFDKMPLENSCSFAEELKFDEYPGREL

QDDDNNEDCDMDGFSDGGYDHYESMIEGINEGGSSQVHFVNDGGEINGAPD

SLSSCDCMSEAFENHGKKDSKNVTQIQQRELLDCDDHSKSSSLDIGADEDLY

YTKTLCAILGNSSSFAQNLCASKSSFVKWKKGGVSERKRPWLQQMMLKKTL

FDVPFMHLSCSSLKLQKENGRKEWTSKLENADNFMGNVFSDKKRESRNIQVL

KSVAPSACEVBKISVLGGTIKYLKNLEARVEELESYMDTTATGARTKRKCPD

VLEQISDNYGPSNIYMGMKKPMINKRKACDIDNIDTGLDIIVSEEDKPLDVKV

NMKEEEVLIEMKCPYREYILYDIMDAINNLHIDAHTVDSSTADGVLTFKLKSK

FRGAATAPVRMIKEALWKVSGKI.

TABLE 6

Partial genomic sequence of cornicul myc gene from *Lotus corniculatus* (birdsfoot trefoil forage).

TAGATGTTGGAATGGAGGGATGGGTTCTACAATGGAGACATTAAGACAATGAAG      (Sequence ID NO: 8)

ACAGTGCAAACCATGGAAACTAAGGCTGATAAAATAGGCCTGCAGAGGAGTGAA

CAACTGAGAGAACTATACAAGTTTCTTCTTGTAGGTGAAGCTGACCCACTAGCTA

AAAGACCTTCTGCTTCATTATCTCCAGAGGATCTCTCAGATTCAGAGTGGTATTAC

TTGGTTTGCATGTCCTTTGTGTTCTACCCCAACCAAAGGTACCATATATGCTCTAA

TTTCATTTAATTCATATAAGGGATTAATTAATGTTTTGTTCTTTATCAATTTTTCT

AGTTTTTTATATTTAACTAAGTTGGGTTTTTCTTTTCTTCTCACAGTTTGCCTGGAA

AAGCACTAGAAACTGGTGAAACAGTGTGGCTATGCAATGCTCAGCAGGCAGATA

GTAAATTTTTCTCTCGTTCTTTGCTAGCAAAGGTTGGATTTTATTCATAAATTTGAT

ATTTTGGTTTTCATATTATATGATGTACGGAGAATGTAAGGTTGATGATATAATAT

GTGGTCCAACCTTGGATTTGGCTCAGTGGGGTAAACATCAATGAGTTTTATGATG

TABLE 6-continued

Partial genomic sequence of cornicul myc gene from *Lotus corniculatus* (birdsfoot trefoil forage).

```
CTCAATTTCTTCCAATAAGCATTGAGCAAGTTGTTCTCTAGAAGAAAGAAATATC
TTTCGCAGTCTTTGATTATATCAAATGTTGGTCAAAAAGTTCTTACGACTAGATAA
AATGTAAGCTAACTTGACCAACATTTAACACAATTAGGTCCATGAGGATTGGCTA
TGTTTTAAAAGACTAACTTGNCCACGGTTACACTTTCAGGAATGAAAATGGCCAT
TAACTCGATTTTTAAAATTTACTAGAATTTAATTTTCATATAGAAATTACTATCCA
TAAATTTTGGGTTTTAAtTcCATYCCCACYTcMCYTTATCTTCTAtTTCATTTTCGGA
AaCCTTTKGGTTTCCNATTTCCCCANATTTTTCCTTATCGCNCCNCTTATCCATACC
ATTATTAATTTATTATTTTTTCCATNCGGTATGACTGACCTCCAATCCNTTTTCCA
CCAATTTTTCTTTTTCTTTTTCCATGTGGACATGGGTTTCAATTGCTGTATCCAGAG
TGCCTCTATTCAGGTATGACATTCTCTCTACACCCTTTTCTATCTAAGGTTAAAAA
TGGTATTTTGTTAGTCGGCATTTGGTTAAAATAACTTAATTAAGTGCTTATGAGCT
TAAAATATAATTGAAGTGCTTATGACGACGAGCGATTATGACANCAAGTTACATA
TATTTTGACAAACCTATGGAAATAAGCTAAAATTATTTGAAAAACTTATTGAAAT
ATGCTCAAAATGTATTGCAAGTAAACCCTTATTCATAAGCTAATTTGAATTTCTTA
TGAAAATAAGTTTAAAATAACTTATAGATAGGCCAAAAGCTATTTAAATATTTTC
TTTCAACTACTTGTATAAGTGTTTGTGCTATTCCACAGAAACTAACTTGAAGTTGG
TGGTAAATATTGGGGTTATTTGGGATTGTGATTATGTCTTAACTAAAAAGGTGAA
ACAAAAGTAAAATGCAAAAGTGAGCTATCTTCAAGGCAAGGGCTGAGTATAGAT
ATTGTGATTTGTACCCTATCCCATATTCTAACTTTACCTTATGACAGAAGCATAGA
TATTAACATTCATACTGTGTGGTGTGTGCTAAAACCTGTTTTTCAGACAGTGGTGT
GTTTTCCCTATCTTGGAGGTGTCATTGAGATAGGAACAACTGAAGxxxxxxTAAAAT
GCCCTTGGAGAACTCATGTTCCTTTGCAGAAGAACTCAAATTTGATGAATATCCT
GGCAGGGAGTTACAAGATGATGATAACAATGAAGATTGTGACATGGATGGATTC
TCTGATGGTGGTTGTGATCATTATGAATCCATGATAGGGGGCATCAACGAGGGTG
GTTCTTCTCAAGTTCATTTTGTGAATGAAGGTGGTGACATCAATGGTGCCCCAGAT
TCCTCTAGTTCTTGTGATTGTAGGTCTGAGGCTTCTGAGAACCATGGTAAGAAGG
ATTCTAAAAATGTAATCCAAATTCAACAAAAGGAGCTTCAAGACTGTGATGATAA
CTCAAAAAGTAGCTCTTTGGATATTGGAGCTGATGAAGATTTGTACTACACAAGA
ACTCTCTGTGCTGTTCTGGGAAATTCATCAAGTTTTGCACAAAATCTATGTGCAAG
TAAATGTAGTTTTGTGAAATGGAATAAGGGAGGAGTTTCTGAAAGGAAGTGGCCG
CGGTTGCAACAAATGATGTTAAAGAAGACTTTGTTTGATGTCCCTTTTATGCACCT
AAGTTGCTCCTCTCTCAAATTACAAAAAGAAAATGGAAGAAAAGAATGGNCTTCT
AAATTGGAAAATGCTGATAATTTCATGGGGAATGTCTTCTCTGATAAGAAAAGAG
AATCTAGAAACATTCAGGTACTCAAATCTGTGGCTCCTTTCTGCATGTGAGGTATT
GGACTTATCATCTGCTGANATTAATGGTATCCCTTCATGANTGGATGNTGGTTGG
AAATTTGCATGCTACAATGCTTAxxxxxxCCTATGGCCCCNGTAATATTTACATGGG
AATGAAAANATCTAGGATAAACAAGAGNAAGGCTTGTGATATTGAT
```

TABLE 7

Two deduced amino acid sequences from portions of the cornicul myc gene
from *Lotus corniculatus* (birdsfoot trefoil).

Fragment A

LEWRDGFYNGDIKTMKTVQTMETKADKIGLQRSEQLRELYKFLLVGEADPL  (Sequence ID NO: 9)

AKRPSASLSPEDLSDSEWYYLVCMSFVFYPNQSLPGKALETGETVWLCNAQQ

ADSKFFSRSLLAKXXXXXXXQTVVCFPYLGGVIEIGTTEXXX

Fragment B

LENSCSFAEELKFDEYPGRELQDDDNNEDCDMDGFSDGGCDHYESMIGGINE  (Sequence ID NO: 10)

GGSSQVHFVNEGGDINGAPDSSSSCSCRSEASENHGKKDSKNVIQIQQKELQD

CDDNSKSSSLDIGADEDLYYTRTLCAVLGNSSSFAQNLCASKSSFVKWNKGG

VSERKWLQQMMLKKTLFDVPFMHLSCSSLKYKKKMEEKNGLLNQKMLIISW

GMSSLIRKENLETFRYSNLWLLSACE

NB: Sequence was deduced from genomic DNA aligned to the complete cDNA from
*Lotus uliginosis*.

TABLE 8

Comparison of amino acid sequences of myc gene product of *Lotus japonicus*
and *L. uliginosis* and product of delila gene of *Antirrynum majus*.

| | | | | | |
|---|---|---|---|---|---|
| *L. uliginosis* | LEWRDGFYNG | DIKTMKTVCT | METKADKIGL | QRSEQLRELY | RFLLEGEADP |
| *L. japonicus* | LEWRDGFYNG | DIKTMKTVQT | METKADKIGL | QRSEQLRELY | KFLLVGEADP |
| *A. majus delila* | LEWGDGFYNG | DIKTRKTVQS | VELNQDQLGL | QRSDQLRELY | ESLSLGETNT |
| *L. uliginosis* | QAKRPSASLS | PEDLSDSEWY | YLVCRVFLFY | PNQSLPGKAL | EIGETVWLCN |
| *L. japonicus* | LAKRPSASLS | PEDLSDSEWY | YLVCMSFVFY | PNQSLPGKAL | ETGETVWLCN |
| *A. majus delila* | QAKRPTAALS | PEDLTDAEWF | FLVCMSFIFN | IGQGLPGRTL | ARNQAVWLCN |
| *L. uliginosis* | AQQADSKFFS | RSLLAK | (SEQ ID NO:22) | | |
| *L. japonicus* | AQQADSKFFS | RSLFFP | (SEQ ID NO:23) | | |
| *A. majus delila* | AHRADTKVFS | RSLLAK | (SEQ ID NO:24) | | |

TABLE 9

Alignment of deduced amino acid sequence of myc genes from *Lotus uliginosis*
(uli myc; SEQ ID NO:25), *Lotus corniculatus* (bird myc; SEQ ID NO:26) and *Lotus japonicus* (jap
myc; SEQ ID NO:27).

```
                                                 .LEWRDGFYNGDIKTM Majority
         |         |         |         |         |         |
         10        20        30        40        50        60
         |         |         |         |         |         |
 1 MAVGJPKHEKKMQQKNLSAQLAVAVRJIQWJYGIFWAPSTTQQRELEWRDGFYNGDIKTM uli myr.PRO
 1 .....................................LEWRDGFYNGDIKTM cornicul myr.PRO
 1 .........................................DGFYNGDIKTM jap myr.PRO KTVQTMETKADKIGLQRSEQLRELYKFLLVGEADPLAKRPSAJLSPEDLSDSEWYYLVCM Majority
         |         |         |         |         |         |
         70        80        90        100       110       120
         |         |         |         |         |         |
61 KTVQTMETKADKIGLQRSEQLRELYKFLLVGEADPLAKRPSAJLSPEDLSDSEWYYLVCM uli myr.PRO
16 KTVQTMETKADKIGLQRSEQLRELYKFLLVGEADPLAKRPSAJLSPEDLSDSEWYYLVCM cornicul myr.PRO
12 KTVQTMETKADKIGLQRSEQLRELYKFLLVGEADPLAKRPSAJLSPEDLSDSEWYYLVCM jap myr.PRO
```

TABLE 9-continued

Alignment of deduced amino acid sequence of myc genes from *Lotus uliginosis*
(uli myc; SEQ ID NO:25), *Lotus corniculatus* (bird myc; SEQ ID NO:26) and *Lotus japonicus* (jap myc; SEQ ID NO:27).

```
        SFVFYPNQSLPGKALETGETVWLCNAQQADSKFFSRSLLAK..SASIQTVVCFPYLGGVI Majority
                 |         |         |         |         |         |
                130       140       150       160       170       180
                 |         |         |         |         |         |
121 SFVFYPNQSLPGKALETGETVWLCNAQQADSKFFSRSLLAK..SASIQTVVCFPYLGGVI uli myr.PRO
 76 SFVFYPNQSLPGKALETGETVWLCNAQQADSKFFSRSLLAKXXXXXXXQTVVCFPYLGGVI cornicul myr.PRO
 72 SFVFYPNQSLPGKALETGETVWLCNAQQADSKFFSRSLLAK..SASIQTVVCFPYLGGVI jap myr.PRO EIGTTEVVS...................................................XX Majority
                 |         |         |         |         |         |
                190       200       210       220       230       240
                 |         |         |         |         |         |
179 EIGTTEVVSEDPNLIQHVXTCFLEVSKPTCSDKSSSAHDKPHDDNXYPTTTKGDHEVFDK uli myr.PRO
136 EIGTTEX.....................................................XX cornicul myr.PRO
130 EIGTTEVVS................................................... jap myr.PRO XXLENSCSFAEELKFDEYPGRELQDDDNNEDCDMDGFSDGGCDHYESMIEGINEGGSSQV Majority
                 |         |         |         |         |         |
                250       260       270       280       290       300
                 |         |         |         |         |         |
239 HPLENSCSFAEELKFDEYPGRELQDDDNNEDCDMDGFSDGGYDHYESMIEGINEGGSSQV uli myr.PRO
145 XXLENSCSFAEELKFDEYPGRELQDDDNNEDCDMDGFSDGGCDHYESMIGGINEGGSSQV cornicul myr.PRO
139 ..LENSCSFAEELKFDEYPGRELQDDDNNEDCDMDGFSDGGCDHYESMIEGINEGGSSQV jap myr.PRO HFVNEGGDINGAPDSSSSCDCRSEASENHGKKDSKNVIQIQQKELQDCDDNSXSSSLDIG Majority
                 |         |         |         |         |         |
                310       320       330       340       350       360
                 |         |         |         |         |         |
299 HFVNDGGEINGAPDSLSSCDCMSEAFENHGKKDSKNVTQIQQRELLDCDDHSXSSSLDIG uli myr.PRO
205 HFVNEGGDINGAPDSSSSCSCRSEASENHGKKDSKNVIQIQQKELQDCDDNSXSSSLDIG cornicul myr.PRO
197 HFVNEGGDINGAPDSSSSCDCRSEASENHGKKDSKNVIQIQQKELQDCDDNSXSSSLDIG jap myr.PRO ADEDLYYTRTLCAVLGNSSSFAQNLCASKSSFVKWNKGGVSERK..WLQQMMLKKTLFDV Majority
                 |         |         |         |         |         |
                370       380       390       400       410       420
                 |         |         |         |         |         |
359 ADEDLYYTKTLCAILGNSSSFAQNLCASKSSFVKWKKGGVSERKRPWLQQMMLKKTLFDV uli myr.PRO
265 ADEDLYYTRTLCAVLGNSSSFAQNLCASKSSFVKWNKGGVSERK..WLQQMMLKKTLFDV cornicul myr.PRO
257 ADEVLYYTRTLCAVLGNSSSFAQNLCASKSSFVKWNKGGVSERK..WLQQMMLKKTLFDV jap myr.PRO PFNHLSCSSLK.YKKKMEEKNGLLNW..KMLIISWGHSSLI..RKENLEXFRYJKSVAPS Majority
                 |         |         |         |         |         |
                430       440       450       460       470       480
                 |         |         |         |         |         |
419 PFMHLSCSSLK.....LQKENGRKEWTSKLENADNFMGNVFSDKKRESRNIQVLKSVAPS uli myr.PRO
323 PFMHLSCSSLK.YKKKMEEKNGLLNQ..KMLIISWGMSSLI..RKENLETFRYSNLWLLS cornicul myr.PRO
315 PFMHLSCSSLKNYKKKMEEKNGLLNW..KMLIISWGMSSLI..RKENLETFRYSKSVAPS jap myr.PRO ACEVEKISVLGXTIXYLKXLEARVEELESYMDTTATGARTXRKCPXVXEQISDNYGPSNI Majority
                 |         |         |         |         |         |
                490       500       510       520       530       540
                 |         |         |         |         |         |
474 ACEVEKISVLGGTIKYLKNLEARVEELESYMDTTATGARTKRKCPDVLEQISDNYGPSNI uli myr.PRO
370 ACE                                                          cornicul myr.PRO
371 ACEVEKISVLGDTIQYLKKLEARVEELESYMDTTATGARTRRKCPRVQEQISDNYGPSNI jap myr.PRO YMGMXXXXINXRKACDIDXIDTGLDIIVSXXXXXXXXXXXXXXXXXXXXXXXXXXXXXX Majority
                 |         |         |         |         |         |
                550       560       570       580       590       600
                 |         |         |         |         |         |
534 YMGMXXPMINKRKACDIDNIDTGLDIIVSEEDKPLDVKVNMKEEEVLIEMKCPYREYILY uli myr.PRO
380 ACE                                                          cornicul myr.PRO
431 YMGMKKSRINKRXACDIDDIDTGLDIIVS............................... jap myr.PRO
```

TABLE 9-continued

Alignment of deduced amino acid sequence of myc genes from *Lotus uliginosis*
(uli myc; SEQ ID NO:25), *Lotus corniculatus* (bird myc; SEQ ID NO:26) and *Lotus japonicus* (jap myc; SEQ ID NO:27).

```
     XXXXXXXXXXXXXXXXXXXXXXXXXXXXXXXXXXFRGAATAPVRMIKEALWKVSGKI.    Majority
             |         |         |         |         |
            610       620       630       640       650
             |         |         |         |         |
594 DIMDAINNLHIDAHTVDSSTADGVLTFKLKSKFRGAATAPVRMIKEALWKVSGKI.        uli myr.PRO
380                                                                cornicul myr.PRO
460 ..........................XXXXXXXFRGAATAPVRMIKEALWKVSGKI.       jap myr.PRO
```

NB: Sequence from *Lotus corniculatus* and *Lotus japonicus* were deduced from genomic fragments aligned to the complete cDNA from *Lotus uliginosis*.
X indicates no majority amino acid;
....indicates a gap in the alignment.

TABLE 10

Comparison of the deduced amino acid sequence of *L. uliginosis* myc gene (SEQ ID NO: 28) to the most closely related myc genes of *Gossypium hirsutum* (cotton; SEQ ID NO:29) and *Zea mays* (maize; SEQ ID NO:30).

```
    MAXGXXX..QEXXXXQXN.....LXXQLAXAVRSIQWSYAIFWSISTTQPGVLEWXDGFYNGDIKTRKTVQSVELXXDQLXLQRSEQLRE Majority
            |         |         |         |         |         |         |         |         |
           10        20        30        40        50        60        70        80        90
            |         |         |         |         |         |         |         |         |
  1 MAVGSPK..HEKKMQQKN.....LSAQLAVAVRSIQWSYGIFWAPSTTQQRELEWRDGFYNGDIKTMKTVQTMETKADKIGLQRSEQLRE uli myc.pro
  1 MSTGVQH..QER..VPMN.....LKKQLALAVRNIQWSYAIFWSISTRQPGVLEWGEGYYNGDIKTRKTVQSVELNTDQLSLQRSEQLRQ Gh delila.prc
  1 MALSASRVQQAEELLQRPAERQLMRSQLAAAARSINWSYALFWSISDTQPGVLTWTDGFYNGEVKTRKISNSVELTSDQLVMQRSDQLRE Maize Lc.pro LYEXLLXGEXDPQAK..RPSASLSPEDLXDTEWYYLVCMSFVFXPGQGLPGRXLXSGEXVWLCNAHXADSKXFXRSLLAKSASIQTXVCF Majority
            |         |         |         |         |         |         |         |         |
          100       110       120       130       140       150       160       170       180
            |         |         |         |         |         |         |         |         |
 84 LYRFLLEGEADPQAK..RPSASLSPEDLSDSEWYYLVCMSFVFYPNQSLPGKALEIGETVWLCNAQQADSKFFSRSLLAKSASIQTVVCF uli myc.pro
 82 LYESLSAGESSPQAK..RPSAALSPEDLTDTEWYYLVCMSFVFNIGQGLPGRTLSSGQPVWLCNAHCADSKVFGRSLLAKSASIQTAVCF Gh delila.prc
 91 LYEALLSGEGDRRAAPARPAGSLSPEDLGDTEWYYVVSMTYAFRPGQGLPGRSFASDEHVWLCNAHLAGSKAFPRALLAKSASIQSILCI Maize Lc.pro PXXGGVXELGTTDXVXEDPXLIQRVKTXFLEX..PXPXXSXRSXXXXXXXXDDXXXXXCXXXDXXXXDK..KMXXXXGCXQXEELXXDEX Majority
            |         |         |         |         |         |         |         |         |
          190       200       210       220       230       240       250       260       270
            |         |         |         |         |         |         |         |         |
172 PYLGGVIEIGTTEVVSEDPNLIQHVKTCFLEV..SKPTCSDKSSAHDKPHDDNKYPTCTKGDHEVFD...KMPLENSCSFAEELKFDEY uli myc.pro
170 PFSGGVVELGVTDLVFEDLSLIQRVKTLLLDD..PQPIVSKRSIQVDGMNND....LACPALDPLILAT..KLSPILGCEQLETVSPDDS Gh delila.prc
181 PVMGGVLELGTTDTVPEAPDLVSRATAAFWEPQCPSSSPSGRANETGEAAADDGTFAFEELDHNNGMDDIEAMTAAGGHGQEEELRLREA Maize Lc.pro PXXXLXXXXXXEDXXXXXF....YXXXXXXMIEGINXGGXSQVXXWXFXXXXFEXNCXXXSLXSXDCXSXXXXXHXKXXPXXRXXXXXXX Majority
            |         |         |         |         |         |         |         |         |
          280       290       300       310       320       330       340       350       360
            |         |         |         |         |         |         |         |         |
257 PGRELQDDDNNEDCDMDGFSDGGYDHYESMIEGINEGGSSQVH...FVNDGGEINGAPDSLSSCDCMSEAFENHGKKDS..KNVIQIQQR uli myc.pro
252 PD.GLEPKQSRED..............SLLIEGIN.GGASQVQSWQFMDEEFS.NCVHHSLNSSDCISQTIADHRKVVPLCRGENDNGLQ Gh delila.prc
271 EALSDDASLEHITKEIEEF....YSLCDEM..DLQALPLPLEDGWTVDASNFEVPCSSP..............QPAPPPVDRATANVA.. Maize Lc.pro XXXXCXDXSKXXSXDX.XXXDXXXXXXLXAXXXXSXXXXXX....XXXXSSFXXWXKXGXXSXXXRDXXPQXXLKKXLFXVPXMHXXXX Majority
            |         |         |         |         |         |         |         |         |
          370       380       390       400       410       420       430       440       450
            |         |         |         |         |         |         |         |         |
342 ELLDCDDHSKSSSLDIGADEDLYYTKTLCAILGNSSSFAQNL....CASKSSFVKWKKGGV.SERKRPWLQQMMLKKTLFDVPFMHLSCS uli myc.pro
325 DVEECN.QTKLTSFDR.QNDDRHFHEVLSALFKSSHPLILGPQFRNSNKESSFIRWQKNGLKPQKERDETPQKLLKKILFLVPHMHDRGL Gh delila.prc
339 .....ADASRAPVYG................................SRATSFMAWTRSSQQSSCSDDAAPAAV.......VPAIEEPQR Maize Lc.pro XLKXXKXXXRXXAWXS........XXEXXXXXXNHVXSERKRREKXNEXXXVLKSLXPSXXXXYXKXSILXXTIXYLKXLERRVXELESXR Majority
            |         |         |         |         |         |         |         |         |
          460       470       480       490       500       510       520       530       540
            |         |         |         |         |         |         |         |         |
427 SLKLQKENGRKE.WTS........KLENADNFMGNVFSDKKRESR...NIQVLKSVAPSACEVEKISVLGGTIKYLKNLEARVEELESYM uli myc.pro
413 IESPETNAVRDAAWRP..........EADEICGNHVLSERKRREKINERLMMLKSLVPANNKADKVSILDVTIEYLQTLERRVAELESCR Gh delila.prc
385 LLK..KVVAGGGAWESCGGATGAAQEMSGTGTKNHVMSERKRREKLNEMFLVLKSLLPSIHRVNKASILAETIAYLKELQRRVQELESSR Maize Lc.pro
```

TABLE 10-continued

Comparison of the deduced amino acid sequence of *L. uliginosis* myc gene (SEQ ID NO: 28) to the most closely related myc genes of *Gossypium hirsutum* (cotton; SEQ ID NO:29) and *Zea mays* (maize; SEQ ID NO:30).

```
    XXXXXXARTKXXXXXXXXERXSDNXGXXXXXXG.KKXXXXSKRKAXDXXDXXDXEXXXVXSXDXXTXXVTVXMXXKEVLIEXKCPWREXILX  Majority
          |         |         |         |         |         |         |         |         |
         550       560       570       580       590       600       610       620       630
          |         |         |         |         |         |         |         |         |
505 DTTATGARTKRKCPDVLEQISDNYGPSNIYMGMKKPMINKRKACDI.DNIDTGLDIIVSEEDKPLDVKVNMKEEEVLIEMKCPYREYILY  uli myc.pro
493 KSE...ARTK......IERTSDNNG........KKSSLSKRKAYDVVDEADQEIGYVASKDGSTDKVTLSMNNKELLIEFKCPWREGILL  Gh delila.pro
473 EPASRPSETTTRLITRPSRGNNESVRKEVCAG......SKRKSPELGRD.DVERPPVLTMDAGTSNVTVTVSDKDVLLEVQCRWEELLMT  Maize Lc.pro XVMDAIXXLHLDXHSVQSSTXDGXLXLKIKSKFXGSXXAXXXMIXEALXKXXGKX.                                    Majority
          |         |         |         |         |
         640       650       660       670       680
          |         |         |         |         |
594 DIMDAINNLHIDAHTVDSSTADGVLTFKLKSKFRGAATAPVRMIKEALWKVSGKI.                                    uli myc.pro
566 EVMDALSILNLDCHSVQSSTTEGILSLTIKSKYKGSSVAKAGPIEQALQRIASK.C                                    Gh delila.pro
556 RVFDAIKSLHLDVLSVQASAPDGFMGLKIRAQFAGSGAVVPWMISEALRKAIGKR                                     Maize Lc.pro
```

NB: Ulimyc has 36-41% identical amino acids to *G. hirsutum delila* (the most similar dicot gene, GenBank Accession number AAK19613), and 30-34% identical amino acids to maize B-Peru (the most similar monocot gene, GenBank Accession number A41388). B-Peru does not function to induce anthocyanin induction in alfalfa. Ulimyc also has 27-29% amino acid identity to maize Lc, which is capable of strong anthocyanin induction in alfalfa (Gruber et al., US provisional patent application).
X indicates no majority amino acid;
....indicates a gap in the alignment.

TABLE 11

DNA primers used to isolate and analyze the Lotus myc gene

| Primer Function | Primer Name | | Sequence (5'-3') |
|---|---|---|---|
| Initial Isolation of Lotus | Reg A (SalI) | SEQ ID NO:11 | GGG TGC T(T/G)A CGT CGA CGG A(C/T)G GGT TCT AC |
| myc PCR fragments | Reg E (BamHI) | SEQ ID NO:12 | GGG ATC GAG AC(G/A) A(T/C)T GTC TGA AT(T/G) GAC GC |
| | Reg F (BclI) | SEQ ID NO:13 | TCC GG(C/A) ACC TGA TCA GTA GTA CCA AGC |
| Isolation of cDNA from *L.* | (myc 1) | SEQ ID NO:14 | CCT ATT TTA TCA GCC TTA GTT TCC |
| *uliginosis* by 3' and 5' | (myc 2) | SEQ ID NO:15 | GTC TTA ATG TCT CCA TTG TAG AAC C |
| RACE | (myc 3) | SEQ ID NO:16 | GGA TCT CTC AGA TTC AGA GTG GTA |
| | (myc 4) | SEQ ID NO:17 | TGG TTT GCA TGT CCT TTG TG |
| Amplification of jap myc | (myc 14) | SEQ ID NO:18 | GGT TCT ACA ATG GAG ACA TTA AGA CAA |
| sequence in *L. japonicus* | (myc 15) | SEQ ID NO:19 | TCT TCC TTA CAG AAA CTC CTC C |
| tan mutants | (myc 16) | SEQ ID NO:20 | ATG AAG ATT GTG ACA TGG ATG G |
| | (myc 17) | SEQ ID NO:21 | ATC AAT ATC ACA AGC CTT CCT CTT |

BIBLIOGRAPHY

Babwah, A., Brown, G. G. and Waddell, C. S. 1998. 11*th* Int.'l Crucifer Genetics Workshop. Quebec, Canada P-31.Damiani, F.; Paolocci, F.; Consonni, G.; Crea, F.; Tonelli, C.; Arcioni, S. A maize anthocyanin transactivator induces pigmentation in hairy roots of dicotyledenous species. *Plant Cell Rep.* 17:339 (1998).

Bae, H.-D., McAllister, T. A., Muir, A. D., Yanke, L. J., Bassendowski, K. A. and Cheng. Y-J. 1993a J. Agric. Food Chem. 41: 1256-1260.

Bac, H.-D., McAllister, T. A., Yanke, J., Cheng, K.-J. and Muir, A. D. 1993b Appl. Environ. Micro. 59: 2132-2138.

Bavage, A. D.; Davies, I. G.; Robbins, M. P.; Morris, P. Expression of an *Antirrhinum* dihydroflavonol reductase gene results in changes in condensed tannin structure and accumulation in root cultures of *Lotus corniculatus* (birdsfoot trefoil). *Plant Mol. Biol.* 35:443 (1997).

Bell, T. A., EtcheRs, J. L., Williams, C. F. and Porter, W. L. 1962. Inhibition of pectinase and cellulase by certain plants. Bot. Gaz. 123: 220-223.

Bradley, J. M.; Davies, K. M.; Deroles, S. C.; Bloor, S. J.; Lewis, D. H. The maize Lc regulatory gene up-regulates the flavonoid biosynthetic pathway of petunia *Plant J.* 13:381 (1998).

Brownlee, H. E., Hedger, J. and Scott, I. M. 1992. Effects of a range of procyanidins on the cocoa pathogen *Crittipellis perniciosa*. Physiol. Mol. Plant Pathol. 40: 227-232.

Butler, L. G. Relative degree of polymerization of sorghum tannin during seed development and maturation. *J. Agric. Food Chem.* 30:090 (1982).

Carron, T. R.; Robbins, M. P.; Morris, P. Genetic modification of condensed tannin biosynthesis in *Lotus corniculatus*. 1. Heterologous antisense dihydroflavonol reductase down-regulates tannin accumulation in hairy root cultures. *Theor. Appl. Genet.* 87:1006 (1994).

Chandler, V. L.; Radicella, J. P.; Robbins, T. P.; Chen. J.; Turks, D. Two regulatory genes of the maize anthocyanin pathway are homologous: Isolation of the B utilizing R genomic sequences. *Plant Cell* 1:1175 (1989).

Charrier, B.; Coronado, C.; Kondorosi, A.; Ratet, P. Molecular characterization and expression of alfalfa (*Medicago sativa* L.) flavanone-3-hydroxylase and dihydroflavonol-4-reductase encoding genes. *Plant Mol. Biol.* 29:773 (1995).

Colliver, S. P.; Morris, P.; Robbins, M. P. Differential modification of flavonoid and isoflavonoid biosynthesis with an antisense chalcone synthase construct in transgenic *Lotus corniculatus. Plant Mol. Biol.* 35:509 (1997).

Cone, K. C.; Burr, F. A.; Burr, B. Molecular analysis of the maize anthocyanin regulatory locus C1. *Proc. Nat'l. Acad. Sci. (USA)* 83:9631 (1986).

Consonni, G.; Geuna, F.; Gavazzi, G.; Tonelli, C. Molecular homology among members of the R gene family in maize. *Plant J.* 3:335 (1993).

Constantino, L., Albasini, A., Rastelli, G. and Benvenuti, S. 1992. Activity of polyphenolic crude extracts as scavengers of superoxide radicals and inhibitors of xanthine oxidase. Planta Med. 58: 342-344.

Damiani, F.; Paolocci, F.; Cluster, P. D.; Arcioni, S.; Tanner, G. J.; Joseph, R. G.; Li, Y. G.; deMajnik, J.; Larkin, P. J. The maize transcription factor Sn alters proanthocyanidin synthesis in transgenic *Lotus corniculatus* plants. *Aust. J. Plant Phys.* 26: in press (1999).

de Majnik, J.; Joseph, R. G.; Tanner, G. J.; Larkin, P. J.; Dmordjevic, M. A.; Rolfe, B. G.; Weinman, J. J. A convenient set of vectors for expression of multiple gene combinations in plants. *Plant Mol. Biol. Rep.* 15:134 (1997).

de Majnik, J.; Tanner, G. J.; Joseph, R. G.; Larkin, P. J.; Weinman, J. J.; Djordjevic, M. A.; Rolfe, B. G. Transient expression of maize anthocyanin regulatory genes influences anthocyanin production in white clover and peas. *Aust. J. Plant Physiol.* 25:335 (1998).

Devic, M.; Guilleniinot, J., Debeaujon, I., Bechtold, N., Bensaude, E., Koornneef, M., Pelletier, G. and Delseny, M. 1999. The BANYULS gene encodes a DFR-like protein and is a marker of early seedcoat development. Plant J. 19: 387-398.

Erdal, K. Proanthocyanidin-free barley. *J. Inst. Brewing* 92:220 (1986).

Falk, D. E. 1985. Genetic studies with proanthocyanidin-free barley. Barley Genetics Newsletter 15: 27-30.

Fay, J. P., Cheng, K. J., Hanna, M. R., Howarth, R. E. and Costerton, J. W. 1980. In vitro digestion of bloat-safe and bloat-causing legumes by rumen microorganisms: Gas and foam production. J. Dairy Sci. 63: 1273-1281.

Furstenburg, D.; van Hoven, W. Condensed tannin as antidefoliate agent against browsing by giraffe (*Giraffa cantelopardalis*) in the Kruger National Park. Comp. Biochem. Physiol. 107A:425 (1994).

Gelvin, S. B. and Schilperoort, R. A. 1991. Plant Molecular Biology Manual. Kluwer Academic Publ. Boston.

Gerats, A. G.; Bussard, J.; Coe, E. H. Fr.; Larson, R. Influence of B and R on UDPG:flavonoid-3-0-glucosyltransferase in *Zea mays. L. Biochem. Genet* 22:1161 (1984).

Glick, B. R. and Thompson, J. E. 1993. Methods in Plant Molecular Biology and Biotechnology. CRC Press. Boca Raton.

Goff, S. A.; Cone, K. C.; Chandler, V. L. Functional analysis of the transcriptional activator encoded by the maize B gene: evidence for a direct functional interaction between two classes of regulatory proteins. *Genes and Development* 6:864.

Goodrich, J.; Carpenter, R.; Coen, E. S. A common gene regulates pigmentation pattern in diverse plant species. *Cell* 68:955 (1992).

Goplen, B. P.; Howarth, R. E.; Sarkar, S. K.; Lesins. K. A search for condensed tannins in annual and perennial species of *Medicago, Trigonella*, and *Onobrychis. Crop Sci.* 20:801(1980).

Grotewold, E.; Does, R. How genes paint flowers and seeds. *Trends in Plant Sci.* 3:212 (1998).

Gruber, M. Y., Ray, H., Auser, P., Skadhauge, B., Falk, J., Thomsen, K. K., Stougaard, J., Muir, A., Lees, G., Coulman, B., McKersie, B., Bowley, S. and von Wettstein, D. 1999. Genetic systems for condensed tannin biotechnology. Invited Book chapter. In: Gross, G. G., Hemingway, R. And Yoshida, T. (Eds.) Plant polyphenols 2: Chemistry and Biology. Plenum Press, New York. In press.

Gruber, M. Y., Skadhauge, B. and Stougaard, J. 1996. Condensed tannin mutations in *Lotus japonicus*. Polyphenol Letters. 18: 4-8.

Howarth, R. E.; Chaplin, R. K.; Cheng, K. -J.; Goplen, B. P.; Hall, J. W.; Hironaka, R.; Majak, W.; Radostits, O. M. Bloat in cattle. Agriculture Canada Publication 1858/E. Communications Branch. Agriculture and Agri-Food Canada, Ottawa (1991).

Hubank, M.; Schatz, D. F. Identifying differences in the mRNA expression by representation difference analysis of cDNA. *Nuci. Acids Res.* 22:5640 (1994).

Jambunathan, R, Butler, L. G., Bandyopadhyay, R. and Mughogho, L. K. 1986. Polyphenol concentrations in grain, leaf, and callus tissues of mold-susceptible and mold-resistant sorghum cultivars. J. Agric. Food Chem. 34: 425-429.

Jende-Strid, B. 1990. Proanthocyanidin-free barley: Genetics, biochemistry and breeding. PhD Thesis. The Royal Veterinary and Agricultural University, Copenhagen.

Jende-Strid, B. Genetic control of flavonoid biosynthesis in barley. *Hereditas* 119:187 (1993). Koorneef, M. Mutations affecting the testa colour in *Arabidopsis. Arabid. Inf Service* 27:1 (1990).

Jones, G. A.; McAllister, T. A.; Muir, A. D.; Cheng, K-D. Effects of sainfoin (*Onobrychis viciifolia* Scop.) condensed tannins on growth and proteolysis by four strains of ruminal bacteria. *Appl. Environ. Microbiol.* 60:1374 (1994).

Joseph, R.; Tanner, G.; Larkin, P. Proanthocyanidin synthesis in the forage legume *Onobrychis viciifohia*. A study of chalcone synthase, dihydroflavonol 4-reductase and leucoanthocyanidin 4-reductase in developing leaves. *Aust. J. Plant Physiol.* 25:27 (1998).

Junghans, H.; Dalkin, K; Dixon, R. A. Stress responses in alfalfa (*Medicago sativa* L.). Part 15. Characterization and expression patterns of members of a subset of the chalcone synthase multigene family. *Plant Mol. Biol.* 22:239 (1993).

Koorneef, M. 1991. The complex syndrome of ttg mutants. Arabidopsis Information Service 18: 45-51.

Koornneef, M., Deliaert, L. W. M. and van der Veen, J. H. 1982. EMS- and radiation-induced mutation frequencies at individual loci in *Arabidopsis thaliana* (L.) Heynh. Mutation Research 93: 109-123.

Koupai-Abyazani, M. R.; McCallum, J.; Muir, A. D.; Bohm, B. A.; Towers, G. H. N.; Gruber, M. Y. Developmental changes in the composition of proanthocyanidins from leaves of sainfoin (*Onobrychis viciifolia* Scop.) as determine by HPLC analysis. *J Agr. Food Chem.* 41:1066 (1993).

Koupai-Abyazani, M. R; McCallum, J.; Muir, A. D.; Lees, G. L.; Bohlu, B. A.; Towers, G. H. N.; Gruber, M. Y. Purification and characterization of a proanthocyanidin polymer from seed of alfalfa (*Medicago sativa* cv. Beaver). *J. Agric. Food Chem.* 41:565 (1993).

Larkin, P. J.; Yuguang, L.; Tanner, G. J.; Banks, P. M. Using alien genes—translocations, transfusions and transgressions. In: Focused Plant Improvement. Towards Responsible and Sustainable Agriculture. *Proc. Tenth Australian Plant Breeding Conference*. Gold Coast, Australia (April) (1993).

Lea, A. G. H. 1992. Flavor, color, and stability in fruit products: The effect of polyphenols. In: Hemingway, R. W.; Laks, P. E. (eds.) Plant Polyphenols: Synthesis, Properties, Significance. Basic Life Sciences vol. 59. Plenum Press, New York.

Lees, G. L. Condensed tannins in some-forage legumes: their role in the prevention of ruminant pasture bloat. In: Hemingway, R. W.; Laks, P. E. (eds.) Plant Polyphenols: Synthesis, Properties, Significance. Plenum Press, New York. pp 914 (1992).

Lees, G. L., Wall, K. M., Beveridge, T. H. and Suttill, N. H. 1995. Localization of condensed tannins in apple fruit peel, pulp, and seeds. Can. J. Bot. 73: 1897-1904.

Li, Y. G., Tanner, G. and Larkin, P. 1996. J. Sci. Food Agric. The DMACA-HCl protocol and the threshold proanthocyanidin content for bloat safety in forage legumes. 70: 89-101.

Liao, H., Cai, Y. and Haslam, E. 1992. Polyphenol Interactions. Anthocyanins: Co-pigmentation and colour changes in red wines. J. Sci. Food Agric. 59: 299-305. Beveridge, T., Harrison, J. E. and Weintraub, S. E. 1997. Procyanidin contributions to haze formation in anaerobically produced apple juice. Food Science and Technology 30: 594-601.

Lloyd, A. M.; Walbot, V.; Davis, R-W. *Arabidopsis* and *Nicotiana* anthocyanin production activated by maize regulators R and C1. *Science* 258:1773 (1992).

Ludwig, S. R.; Habera, L. F.; Dellaporta, S. L.; Wessler, S. R. Lc, a member of the maize R gene family responsible for tissue-specific anthocyanin production encodes a protein similar to anthocyanin transcriptional activators and contains the myc-homology region. *Proc. Nat'l. Acad. Sci. (USA)* 86:7092 (1989).

Mangan, J. L. 1988. Nutritional effects of tannins in animal feeds. Nutr. Res. Rev. 1: 209-231. Hagerman, A. E. and Butler, L. G 1981. The specificity of proanthocyanidin-protein interactions. J. Biol. Chem.256: 4494-4497.

Manuwoto, S.; Scriber, J. M. Effects of hydrolyzable and condensed tannin on growth and development of two species of polyphagous lepidoptera: *Spodoptera eridania* and *Callosamia promethea*. *Oecologia* (Berlin) 69:225 (1986).

McNabb, W. C., Waghor, G. C., Barry, T. N. and Shelton, I. D. 1993.) The effect of condensed tannins in *Lotus pedunculatus* on the digestion and metabolism of methionine, cystine and inorganic sulphur in sheep. Brit. J. Nutrition 70: 647-661.

Meldgaard, M. Expression of chalcone synthase, dihydroflavonol reductase and flavanone-3-hydroxylase in mutants of barley deficient in anthocyanin and proanthocyanidin biosynthesis. *Theor. Appl. Genet.* 83:695 (1992).

Min, B. R.; Barry, T. N.; McNabb, W. C.; Kamp, P. D. Effect of condensed tannins on the production of wool and on its processing characteristics in sheep grazing *Lotus corniculatus*. *Aust. J. Agric. Res.* 49:597 (1998).

Mooney, M.; Desnos, T.; Harrison, K.; Jones, J.; Carpenter, R.; Coen, E. Altered regulation of tomato and tobacco pigmentation genes caused by the delila gene of *Antirrhinum*. *Plant J.* 7:333 (1995).

Morris, P.; Robbins, M. P. Condensed tannin formation by *Agrobacterium rhizogenes* transformed root and shoot organ cultures of *Lotus corniculatus*. *J. Exp. Bot.* 43: 221 (1992).

Moyano, E.; Martinez-Garcia, M. F.; Martin, C. Apparent redundancy in myb gene function provides gearing for the control of flavonoid biosynthesis in *Antirrhinum* flowers. *Plant Cell* 8:1519 (1996).

Muir, A. D. 1997. Antioxidative activity of condensed tannins. In: Shahidi, F. Natural Antioxidants. Chemistry, Health Effects, and Applications. AOCS Press, Champaign, Ill. Pp. 204-212.

Muir, A. D., Gruber, M. Y., Hinks, C. F., Lees, G. L., Onyilagha, J., Hallett, R., Xia, F., Soroka, J. and Erlandson, M. 1999. The effect of condensed tannin in the diets of major crop insects. Book chapter. In: Gross, G. G., Hemingway, R. and Yoshida, T. Eds.) Plant Polyphenols 2: Chemistry and Biology. Plenum Press, New York. In press.

Naczk and Shahidi, 1992. In: Hemingway, R. W.; Laks, P. E. (eds.) Plant Polyphenols: Synthesis, Properties, Significance. Plenum Press, New York.

Newman, R. K.; Newman, C. W.; El-Negoumy, A. M.; Aastrup, S. Nutritive quality of proanthocyanidin-free barley. *Nutrition Reports Int'l*. 30:809 (1984).

Niezen, K. E.; Waghorn, T. S.; Charleston, W. A. G.; Waghorn, G. C. Growth and gastrointestinal nematode parasitism in lambs grazing either lucerne (*Medicago sativa*) or sulla (*Hedysarum coronarium*) which contains condensed tannins. *J. Agric. Sci.* (Cambridge) 125:81 (1995).

Olah, A. F. and Sherwood, R. T. 1971. Phytopathology 61: 65-69.

Olson, O.; Wang, X.; von Wettstein, D. Sodium azide mutagenesis: Preferential generation of A:T-G:C transitions in the barley Ant18 gene. *Proc. Nat'l. Acad. Sci. USA* 90:8043 (1993).

Outtrup, H. 1992. Proanthocyanidins, the brewing process, and the quality of beer. In: Herningway, R. W.; Laks, P. E. (eds.) Plant Polyphenols: Synthesis, Properties, Significance. Basic Life Sciences vol. 59. Plenum Press, New York.

Paz-Arez, J.; Ghosal, D.; Weinard, U.; Peterson, P.; Saedler, H. The regulatory C1 locus of *Zea mays* encodes a protein with homology to myb proto-oncogene products and with structural similarities to transcriptional activators. *EMBO J.* 6:3553 (1987).

Petersen, M., Strack, D. and Matern, U. 1999. Biosynthesis of phenylpropanoids and related compounds. In: Wink, M. (Ed.) Biochemistry of plant secondary metabolism. Annual Plant Reviews 2: 151-221.

Polya, G. M. and Foo, L. Y. 1994. Inhibition of eukaryote signal-regulated protein kinases by plant-derived catechin-related compounds. Phytochem. 35: 1399-1405.

Porter, L. J. Flavans and proanthocyanidins. In: Harborne, J. B. (ed.) The Flavonoids. Advances in Research Since 1980. Chapman and Hall, New York. pp. 21 (1988).

Quattrocchio, F.; Wing, J. F.; Leppen, H. T. C.; Mol, J. N. M.; Koes, R. E. Regulatory genes controlling anthocyanin pigmentation are functionally conserved among plant species and have distinct sets of target genes. *Plant Cell* 5:1497 (1993).

Quattrocchio, F. M. Regulatory genes controlling flower pigmentation in *Petunia hybrida*. PhD dissertation. Vrije Universiteit, Amsterdam, The Netherlands (1994).

Quattrocchio, R.; Wing, J. F.; van der Woude, K.; Mol, J. N. M.; Koes, R. Analysis of bHLH and myb domain proteins: species specific regulatory differences are caused by divergent evolution of target anthocyanin genes. *Plant J.* 13:475 (1998).

Reddy, V. S.; Dash, S.; Reddy, A. R. Anthocyanin pathway in rice (*Orza sativa* L.): identification of a mutant showing dominant inhibition of anthocyanins in leaf and accumulation of proanthocyanidins in pericarp. *Theor. Appl. Genet.* 91:301 (1995).

Reed, J. D. 1987. Phenolics, fiber, and fiber digestibility in bird resistant and non-bird resistant sorghum grain. J. Agric. Food Chem. 35: 461-464.

Robbins, M. P.; Bavage, A. D.; Strudwicke, C.; Morris, P. Genetic manipulation of condensed tannins in higher plants. II. Analysis of birdsfoot trefoil plants harboring antisense dihydroflavonol reductase constructs. *Plant Physiol.* 116:1133 (1997).

Sablowski, R. W. M.; Moyano, B.; Cullianezmacia, F. A.; Schuch, W.; Martin, C.; Beven, M. A flower-specific MYB protein activates transcription of phenylpropanoid biosynthetic genes. *EMBO J.* 13:128 (1994).

Saleli, N. A. M, Boulos, L., El-Negoumy, S. I. and Abdalla, M. F. 1982. Biochem. Syst. Ecol. 10: 33-36.

Shirley, B. W. Flavonoid synthesis: "new functions" for an "old pathway." *Trends in Plant Sci.* 1:377 (1996).

Simbaya, J., Slominski, B. A., Rakow, G., Campbell, L. D., Downey, R. K and Bell, J. M. 1995. Quality characteristics of yellow-seeded *Brassica* seed meals: Protein, carbohydrates and dietary fiber components. J. Agric. Food Chem. 43: 2062-2066.

Singh, S.; McCallum, J.; Gruber, M. Y.; Towers, G. H. N.; Muir, A. D.; Bohm, B. A.; Koupai-Abazani, M. R.; Glass, A. D. M. Biosynthesis of flavan-3-ols by leaf extracts of *Onobiychis viciifolia*. *Phytochemistry* 44:425 (1997).

Singleton, V. L. 1992. Tannins and the qualities of wine. In: Hemingway, R. W.; Laks, P. E. (eds.) Plant Polyphenols: Synthesis, Properties, Significance. Basic Life Sciences vol. 59. Plenum Press, New York.

Skadhauge, B. Genetics and biochemistry of proanthocyanidin biosynthesis and their biological significance in crop plants. PhD thesis. The Royal Veterinary and Agriculture University, Copenhagen, Denmark (1996).

Skadhauge, B.; Gruber, M. Y.; Thomsen, K K; von Wettstein, D. Leucocyanidin reductase activity and accumulation of proanthocyanidins in developing legume tissue. *Am. J. Botany* 84:494 (1997).

Skadhauge, B.; Thomsen, K. K.; von Wettstein, D. The role of the barley testa layer and its flavonoid content in resistance to *Fusarium* infections. *Hereditas* 126:147 (1997).

Tamagnone, L.; Merida, A.; Parr, A; Mackay, S.; Culliznez-Macia, F. A.; Roberta, K.; Martin, C. The AmMYB308 and AmMYB330 transcription factors from *Antirrhinum* regulate phenylpropanoid and lignin biosynthesis in transgenic tobacco. *Plant Cell* 10:135 (1998).

Tanner, G. J.; Kristiansen, K. N. Synthesis of $^3$H-3,4-cis-leucocyanidin and enzymatic reduction to catechin. *Anal. Biochem.* 209:274 (1993).

Tanner, G. J.; Kristiansen, K. N.; Jende-Strid, B. Biosynthesis of proanthocyanidins (condensed tannins) in barley. *Proc. XVI Int. Conf Groupe Polypheitols*, Portugal (1992).

Tanner, G. J.; Moate, P.; Dailey, L.; Laby, R.; Larkin, P. J. Proanthocyanidins (condensed tannins) destabilise plant protein foams in a dose dependent manner. Aust. J. Agric. Res. 46:1011 (1995).

Tanner, G. J.; Moore, A. E.; Larkin, P. J. Proanthocyanidins inhibit hydrolysis of leaf proteins by rumen microflora in vitro. *Brit. J. Nuir.* 71: 47 (1994).

Treutter, D. and Feucht, W. 1990. The pattern of flavan-3-ols in relation to scab resistance of apple cultivars. J. Hort. Sci. 65: 511-517.

Von Wettstein, D.; Jende-Strid, B.; Ahrenst-Larsen, B.; Sorensen, J. A. Biochemical mutant in barley renders chemical stabilization of beer superfluous. *Carlsberg Res. Commun.* 42:341 (1979).

Waghorn, G. C., Reed, J. D. and Ndlovu, L. R. 1997. Condensed tannins and herbivore nutrition. Abstracts. Proc. Grasslands 2000. XVIII Int'l Grasslands Congress. Winnipeg/Saskatoon, Canada. Vol. 31, Session 8.

Wang, X.; Olsen, O.; Knudsen, S. Expression of the dihydroflavonol reductase gene in an anthocyanin-free barley mutant. *Hereditas* 119:67 (1993).

Watterson, J. J.; Butler, L. G. Occurrence of an unusual leucoanthocyanidin and absence of proanthocyanidins in *Sorghum* leaves. *J. Agric. Food Chem.* 31:41 (1983).

Wong, J. R; Walker, L. S.; Drikeilis, H.; Klein, T. M. Anthocyanin regulatory genes from maize B-Peru and C1 activate the anthocyanin pathway in wheat, barley and oat cells. *J. Cell Biochem. Suppl.* 0(15 part A):159 (1991).

Zhang, J., Takahashi, K-, Kono, Y., Suzuki, Y., Takeuchi, S., Shimizu, T., Yamaguchi, I., Chijimatsu, M., Sakurai, A., Sato, Y. and Kitamura, H. 1990. Bioactive condensed tannins from bark: Chemical properties, enzyme inhibition and anti-plant-viral activities. J. Pesticide Sci. 15: 585-591.

Gruber, M. Y., Ray, H., Auser, P., Skadhauge, B., Falk, J., Thomsen, K. K., Stougaard, J., Muir, A., Lees, G., Coulman, B., McKersie, B., Bowley, S. and von Wettstein, D. 1998. Genetic systems for condensed tannin biotechnology. In: Gross, G. G., Hemingway, R and Yoshida, T. (Eds.) Plant polyphenols 2: Chemistry and Biology. Kluwer Academic/Plenum Publishers, New York. pp 315-341.

Gruber, M. Y., Ray, H. and Blahut-Beatty, L. 2000. Genetic manipulation of condensed tannin synthesis in forage crops". $2^{nd}$ International Symposium. Molecular Breeding of Forage Crops 2000. Plenum Press. In Press.

Lees, G. L.; Hinks, C. F.; Suttill, N. H. Effect of high temperature on condensed tannin accumulation in leaf tissues of big trefoil (*Lotus uliginosis* Schkuhr). *J. Sci. Food Agric.* 65:415 (1994).

Lees, G. L.; Suttill, N. H.; Gruber, M. Y. Condensed tannins in sainfoin. 1. A histological and cytological survey of plant tissues. *Can. J. Bot.* 71:1147 (1993).

Goff, S. A.; Cone, K. C.; Fromm, M. E. Identification of functional domains in the maize transcriptional activator C1: comparison of wildtype and dominant inhibitor proteins. *Genes and Development* 5:298 (1991).

All publications, patents, and patent applications are incorporated by reference herein, as though individually incorporated by reference.

We claim:

1. An isolated nucleic acid comprising:
   (a) a nucleotide sequence SEQ ID NO: 2; or
   (b) a nucleotide sequence having at least 80% sequence identity to the nucleotide sequence of SEQ ID NO:2, wherein the nucleotide sequence having at least 80% sequence identity encodes a myc-like regulatory protein.

2. The nucleic acid according to claim 1, wherein said nucleic acid sequence is selected from the group consisting of DNA, genomic DNA, cDNA, RNA, and mRNA.

3. A method for inducing or increasing condensed tannin synthesis in a plant comprising:
   (a) transforming a plant with an isolated nucleic acid of claim 1; or with an isolated nucleic acid encoding amino acid sequence SEQ ID NO: 7; and
   (b) selecting a transformed plant wherein the nucleic acid is expressed, whereby condensed tannin synthesis is increased in the plant.

4. An isolated nucleic acid molecule comprising a nucleic acid sequence encoding a protein or peptide capable of increasing production of condensed tannins or anthocyanins in plant cells and tissues expressing such, wherein the nucleic acid sequence is selected from the group consisting of:
   (a) a nucleic acid sequence encoding a protein comprising the amino acid sequence of SEQ ID NO: 7;
   (b) a nucleic acid sequence SEQ ID NO: 2;
   (c) a nucleic acid molecule that has at least 80% sequence identity to the coding region of (a) or (b), wherein the nucleic acid molecule that has at least 80% sequence identity encodes a myc-like regulatory protein;
   (d) a fragment of the nucleic acid sequence of (a), or (b), wherein the fragment encodes a protein which alters the phenylpropanoid/flavonoid pathway leading to increased production of condensed tannins or anthocyanins; and
   (e) a nucleic acid sequence that deviates from (a), (b), (c), or (d) due to the degeneracy of the genetic code.

5. The isolated nucleic acid molecule according to claim 4, wherein the nucleic acid molecule is a cDNA molecule.

6. The isolated nucleic acid molecule according to claim 4, wherein the nucleic acid sequence encodes a protein comprising the amino acid sequence of SEQ ID NO: 7.

7. The isolated nucleic acid molecule according to claim 4, wherein the nucleic acid molecule is an RNA molecule.

8. A vector comprising the nucleic acid molecule of claim 4.

9. The vector according to claim 8, wherein said nucleic acid molecule is linked in sense-orientation to regulatory elements that enable transcription of the nucleic acid molecule and translation of the protein encoded therein in a prokaryotic or a eukaryotic cell.

10. A host cell comprising a heterologous nucleic acid molecule of claim 4, or comprising a vector comprising said nucleic acid molecule, or a cell that is derived from the host cell.

11. A transgenic plant cell comprising a heterologous nucleic acid molecule of claim 4, or comprising a vector comprising the nucleic acid molecule, wherein the nucleic acid molecule is placed under the control of regulatory elements to allow the transcription of a translatable mRNA in plant cells.

12. A transgenic plant comprising the transgenic plant cell according to claim 11.

13. A seed from the transgenic plant of claim 12.

14. The transgenic plant cell according to claim 11, wherein said plant is selected from any plant which expresses any genes of the phenylpropanoid/flavonoid pathway.

15. The transgenic plant according to claim 14, wherein the plant is selected from the group consisting of alfalfa, sweetclover, red clover, white clover, alsike clover, subterrain clover, *brassica*, pea, lentil and soybean.

16. A propagation material of a plant comprising the plant cell according to claim 11.

17. A vector comprising the nucleic acid molecule according to claim 5.

18. A host cell comprising the heterologous nucleic acid molecule according to claim 5 or comprising a vector comprising said nucleic acid molecule.

19. A transgenic plant cell comprising a DNA molecule introduced into said plant cell, wherein said DNA molecule is selected from the group consisting of:
   (a) a DNA molecule coding for a protein comprising amino acid sequence SEQ ID NO: 7;
   (b) a DNA molecule comprising nucleotide sequence SEQ ID NO:2;

(c) a DNA molecule the sequence of which is degenerate as a result of the genetic code compared to the sequence of the DNA molecule of (a), or (b);
(d) a DNA molecule that is complementary to the sequence of the DNA molecule Of (a), (b), or (c); and
(e) a recombinant DNA molecule comprising the DNA molecule according to any one of the DNA molecules of (a), (b), (c), or (d).

20. A transgenic plant regenerated from the plant cell according to claim 19.

21. The transgenic plant cell according to claim 19, wherein said DNA molecule codes for a protein comprising amino acid sequence of SEQ ID NO: 7.

22. A transgenic plant regenerated from the plant cell according to claim 21.

23. The transgenic plant cell according to claim 19, wherein the DNA molecule comprises the nucleotide sequence of SEQ ID NO:2.

24. A transgenic plant regenerated from the plant cell according to claim 23.

25. The transgenic plant according to claim 20, wherein said DNA molecule codes for a protein comprising the amino acid sequence of SEQ ID NO:7.

26. The transgenic plant according to claim 20, wherein said DNA molecule comprises the nucleotide sequence of SEQ ID NO:2.

27. A seed from the transgenic plant according to claim 25, wherein the seed comprises said DNA molecule.

28. A seed from the transgenic plant according to claim 26, wherein the seed comprises said DNA molecule.

29. A transgenic plant comprising a recombinant nucleic acid sequence of SEQ ID NO: 2, wherein expression of said sequence results in an alteration of the phenylpropanoid/flavonoid pathway leading to increased production of condensed tannins or anthocyanins.

* * * * *

SEQUENCE LISTING

<160> NUMBER OF SEQ ID NOS: 21

<210> SEQ ID NO 1
<211> LENGTH: 518
<212> TYPE: DNA
<213> ORGANISM: Lotus uliginosis
<220> FEATURE:
<221> NAME/KEY: misc_feature
<222> LOCATION: (1)...(518)
<223> OTHER INFORMATION: n = A,T,C or G

<400> SEQUENCE: 1

```
ggaatggagg gatgggttct acaatggaga cattaagacn nnnnnnnnnn nggggtgatg      60
ggttctacaa tggagacatt aagacaatga agacagtgca aaccatggaa actaaggctg     120
ataaaatagg cctgcagagg agtgaacaac tgagagaact atacaggttt cttcttgaag     180
gtgaagctga cccacaagct aaaagacctt ctgcttcatt atctccagag gatctctcag     240
attcagagtg gtattacttg gtttgcatga tcctttgtgt tctatcccaa ccaaaggtac     300
catatatgct cttatctcat taattcata tagggattaa ttaatgattt gtttctttgt      360
aaattttttct agtttttta tatttaaaca tgtagagttt ttcttttctt ctcacacagt     420
ttgcctggaa aagcactaga aattggtgaa acagtgtggc tatgcaatgc tcagcaagca     480
gatagtaaat ttttctctcg ttctttgcta gcgaaggt                             518
```

<210> SEQ ID NO 2
<211> LENGTH: 2118
<212> TYPE: DNA
<213> ORGANISM: Lotus uliginosis

<400> SEQUENCE: 2

```
gtgatgacta gtactactct atacactgaa agtaaccgaa gtgaatttga gcagtgttgt      60
aatgccattt actgttgact gtctgaaagt aaacaagcaa agctagcagg agaagaatgg     120
ccgttgggag cccaaagcat gagaagaaga tgcagcaaaa gaacctgagt gcacaactag     180
ctgttgctgt cagaagtatt caatggagct atggaatttt ctgggcacct tcaactactc     240
aacaaagaga actggaatgg agggatgggt tctacaatgg agacattaag acaatgaaga     300
cagtgcaaac catggaaact aaggctgata aaataggcct gcagaggagt gaacaactga     360
gagaactata caggtttctt cttgaaggtg aagctgaccc acaagctaaa agaccttctg     420
cttcattatc tccagaggat ctctcagatt cagagtggta ttacttggtt tgcatgtcct     480
ttgtgttcta tcccaaccaa agtttgcctg gaaaagcact agaaattggt gaaacagtgt     540
ggctatgcaa tgctcagcaa gcagatagta aattttctc tcgttctttg ctagcgaaga     600
gtgcctctat tcagacagtg gtgtgttttc cctatcttgg aggcgtcatt gagataggaa     660
caactgaagt ggtatctgag gatcctaatc tcattcaaca tgtgaagaca tgcttcttag     720
aagtctcaaa gcctacatgc tctgacaaat catcctctgc ccatgacaaa ccacatgatg     780
acaacaaata tccaacatgc actaagggtg accatgaggt gtttgacaaa atgcccttgg     840
agaactcatg ttcctttgca gaagaactca aatttgatga atatcctggc agggaattac     900
aagatgatga taacaatgaa gattgtgaca tggatgggtt ctctgatggt ggttatgacc     960
attatgaatc catgatagag ggcatcaatg agggtggttc ttctcaagtt catttttgtga    1020
atgatggtgg tgaaatcaat ggtgcccag attccttgag ttcttgtgat tgtatgtctg     1080
aggcttttga gaaccatggt aagaaggatt ctaaaaatgt aacccaaatt caacaaaggg    1140
```

-continued

| | |
|---|---|
| agcttctaga ctgtgatgat cactcaaaaa gtagctcttt ggatattgga gctgatgaag | 1200 |
| atttgtacta cacaaaaact ctctgtgcta ttctgggaaa ttcatcaagt tttgcacaaa | 1260 |
| atctatgtgc aagtaaatct agttttgtga aatggaagaa aggaggagtt tctgaaagga | 1320 |
| agaggccgtg gttgcaacaa atgatgttaa agaagacttt gtttgatgtc ccttttatgc | 1380 |
| acctaagttg ctcctctctc aaattacaaa aagaaaatgg cagaaaagaa tggacttcta | 1440 |
| aattggaaaa tgctgataat ttcatgggga atgtcttctc tgataagaaa agagaatcta | 1500 |
| gaaacattca ggtactcaaa tctgtggctc cttctgcatg tgaggtggag aagatttcag | 1560 |
| ttcttggtgg cacaattaaa tacttgaaaa atcttgaggc aagagtggaa gaactagaat | 1620 |
| cttacatgga cactacagct actggagcaa gaaccaaaag aaaatgccca gatgtgctag | 1680 |
| agcagatatc agataactat ggccccagta atatttacat gggaatgaaa aaacctatga | 1740 |
| taaacaagag gaaggcttgt gatattgata acatagacac agggctagac ataattgttt | 1800 |
| ctgaagaaga taagccattg gatgtgaaag tcaacatgaa ggaggaagag gttctgattg | 1860 |
| agatgaaatg tccttacagg gaatacatat tgtatgatat catggatgcc ataaacaatc | 1920 |
| tgcatataga tgcacacaca gttgattcat caacagctga tggtgttctc acatttaaac | 1980 |
| ttaaatccaa gtttcgagga gcagcaactg cgccagtgcg gatgatcaaa gaagcactct | 2040 |
| ggaaagtatc tggaaagatt tgaaatgcct gattgagttt ctcatggaag tagtagattc | 2100 |
| ttctaattgg atccaaaa | 2118 |

<210> SEQ ID NO 3
<211> LENGTH: 2877
<212> TYPE: DNA
<213> ORGANISM: Lotus uliginosis
<220> FEATURE:
<221> NAME/KEY: misc_feature
<222> LOCATION: (1)...(2877)
<223> OTHER INFORMATION: n = A,T,C or G

<400> SEQUENCE: 3

| | |
|---|---|
| gcgggatttg tgrggtgatg ggttctacaa tggagacatt aagacaatga agacagtgca | 60 |
| aaccatggaa actaaggctg ataaaatagg cctgcagagg agtgaacaac tgagagaact | 120 |
| atacaagttt cttcttgtag gtgaagctga cccactagct aaaagacctt ctgcttcatt | 180 |
| atctccagag gatctctcag attcagagtg gtattacttg gtttgcatgt cctttgtgtt | 240 |
| ctaccccaac caaagtttgc ctggaaaagc actagaaact ggtgaaacag tgtggctatg | 300 |
| caatgctcag caggcagata gtaaattttt ctctcgttct ttgctagcaa agagtgcttc | 360 |
| tattcagaca gtggtgtgtt ttccctatct ggaggtgtc attgagatag gaacaactga | 420 |
| agtggtatct gatrtggcta tgcaaygctc agcaggcaga tagtaaattt ttctctcgtt | 480 |
| ctttgctagc aaaggttgga ttttattcat aaatttgata ttttggtttt catattatat | 540 |
| gatgtacgga caatgtaagg ttgatgatat aatatgtggc caaccttgga tttggctcag | 600 |
| tggggtaaac atcaatgggt tttatgatgc tcaatttcgt cctgtaagca ttgagcaagt | 660 |
| tggtctctan aagaaataaa tatctttcgc agtctttgat tgtatcnaat ggtgggcaaa | 720 |
| aaaggttctt acgactaaga taaaaatggn ggttttagac aaaattccca tggagaactc | 780 |
| atgttccttt gcagaagaac tcaaatttga tgaatatcct ggcagggagt tacaagatga | 840 |
| tgataacaat gaagattgtg acatggatgg attctctgat ggtggttgtg atcattatga | 900 |
| atccatgata gagggcatca acgagggtgg ttcttctcaa gttcattttg tgaatgaagg | 960 |

```
tggtgacatc aatggtgccc cagattcctc tagttcttgt gattgtaggt ctgaggcttc    1020
tgagaaccat ggtaagaagg attctaaaaa tgtaatccaa attcaacaaa aggagcttca    1080
agactgtgat gataactcaa aaagtagctc tttggatatt ggagctgatg aagttttgta    1140
ctacacaaga actctctgtg ctgttctggg aaattcatca agttttgcac aaaatctatg    1200
tgcaagtaaa tctagttttg tgaaatggaa taaaggagga gtttctgaaa ggaagtggcc    1260
gcggttgcaa caaatgatgt taaagaagac tttgtttgat gtccctttta tgcacctaag    1320
ttgctcctct ctcaaattac aaaaagaaaa tggaagaaaa gaatggactt ctaaattgga    1380
aaatgctgat aatttcatgg ggaatgtctt ctctgataag aaaagagaat ctagaaacat    1440
tcaggtgggg aagatttcag ttcttggtga cacaattcaa tacttgaaaa agcttgaggc    1500
aagagtggaa gaactagaat cttacatgga cactacagct actggagcaa gaaccagaag    1560
aaaatgcccc agatgtgcta gagcagaaat cactaatgcg ggcccctgca ggtccaccat    1620
atgggatcat ctgctgaaat taatggtatc actcgatgag tgatgtggct gggaaattgc    1680
atgctacaat gctaatgggc taattaaat cttaaaatct ttagttattt ccgtattang    1740
gkcccaagta ttnaaatttt tttacmcctc cattcmcatg gnargttatt ttarcmatag    1800
tgtcctgttc tgttctgaaa ttttatttat taggaatat caaagttcaa tctcaaaaag    1860
cagtgaaaca tgttaaggaa ccagttgtta tgtttgtaaa tttgacagat ttagactctt    1920
tttagcaatt tctaaatgat gtcatatgta gtaagaagtt aacaaaaccc ttgaagttac    1980
tttgtaaata ttgaaatata ttcatgttaa ttgctaacta tgtgaaggtg agaagatt t   2040 cagttcttgg tgacacaatt caatacttga aaagcttga ggcaagagtg gaagaactag    2100
aatcttacat ggacactaca gctactggag caagaaccag aagaaaatgc ccagatgtgc    2160
aagagcagat atcagataac tatggcccca gtaatattta catgggaatg aaaaaatcta    2220
ggataaacaa gaggaaggct tgtgatattg atgacataga cacagggcta gacataattg    2280
tttcannnnn ngccactgcg cntgagaaaa aaccaaattt tatggaatat tattgacatg    2340
tgatcacttt taataatgta ttccnacgtt gttttggct tccctctacc ccatttccca    2400
ggacttgaag aaaccatgta atcaaccctt gtctcgatgc ctccaaaagt cttctttgta    2460
agctacatgc ctataactgc taaaagaatt cttccaaaaa gtagcatgtt taagaccttg    2520
ttccaagtta tctcagtcaa cctgttttga gggggcattc taaccatttg ttacttaacc    2580
ctagcttgaa gggaagagaa gagcatgtta ctcatggact aagacattat caaaaaagat    2640
tttgaccatt gaaagtcatt tatttaatga gtaatttgaa aaattatact tggaagttag    2700
ttttcttttc ttcaatactt gaaagaaat ttgaattctt aaaacttcat ttcagtttcg    2760
aggagcagca actgcgccag tgcggatgat caaagaagca ctctggaaag tatctggaaa    2820
gatttgaaat gcctgattga gtgtctcatg gaagtagtag attcttaatt ggatcca       2877
```

<210> SEQ ID NO 4
<211> LENGTH: 138
<212> TYPE: PRT
<213> ORGANISM: Lotus japonicus

<400> SEQUENCE: 4

Asp Gly Phe Tyr Asn Gly Asp Ile Lys Thr Met Lys Thr Val Gln Thr
 1               5                  10                  15

Met Glu Thr Lys Ala Asp Lys Ile Gly Leu Gln Arg Ser Glu Gln Leu
             20                  25                  30

Arg Glu Leu Tyr Lys Phe Leu Leu Val Gly Glu Ala Asp Pro Leu Ala

-continued

```
                35                  40                  45
Lys Arg Pro Ser Ala Ser Leu Ser Pro Glu Asp Leu Ser Asp Ser Glu
 50                  55                  60

Trp Tyr Tyr Leu Val Cys Met Ser Phe Val Phe Tyr Pro Asn Gln Ser
 65                  70                  75                  80

Leu Pro Gly Lys Ala Leu Glu Thr Gly Glu Thr Val Trp Leu Cys Asn
                 85                  90                  95

Ala Gln Gln Ala Asp Ser Lys Phe Phe Ser Arg Ser Leu Leu Ala Lys
                100                 105                 110

Ser Ala Ser Ile Gln Thr Val Val Cys Phe Pro Tyr Leu Gly Gly Val
                115                 120                 125

Ile Glu Ile Gly Thr Thr Glu Val Val Ser
                130                 135

<210> SEQ ID NO 5
<211> LENGTH: 321
<212> TYPE: PRT
<213> ORGANISM: Lotus japonicus
<220> FEATURE:
<221> NAME/KEY: VARIANT
<222> LOCATION: (1)...(321)
<223> OTHER INFORMATION: Xaa = Any Amino Acid

<400> SEQUENCE: 5

Leu Glu Asn Ser Cys Ser Phe Ala Glu Glu Leu Lys Phe Asp Glu Tyr
 1               5                  10                  15

Pro Gly Arg Glu Leu Gln Asp Asp Asn Asn Glu Asp Cys Asp Met
             20                  25                  30

Asp Gly Phe Ser Asp Gly Gly Cys Asp His Tyr Glu Ser Met Ile Glu
             35                  40                  45

Gly Ile Asn Glu Gly Gly Ser Ser Gln Val His Phe Val Asn Glu Gly
             50                  55                  60

Gly Asp Ile Asn Gly Ala Pro Asp Ser Ser Ser Cys Asp Cys Arg
 65                  70                  75                  80

Ser Glu Ala Ser Glu Asn His Gly Lys Lys Asp Ser Lys Asn Val Ile
                 85                  90                  95

Gln Ile Gln Gln Lys Glu Leu Gln Asp Cys Asp Asp Asn Ser Lys Ser
                100                 105                 110

Ser Ser Leu Asp Ile Gly Ala Asp Glu Val Leu Tyr Tyr Thr Arg Thr
                115                 120                 125

Leu Cys Ala Val Leu Gly Asn Ser Ser Ser Phe Ala Gln Asn Leu Cys
                130                 135                 140

Ala Ser Lys Ser Ser Phe Val Lys Trp Asn Lys Gly Gly Val Ser Glu
145                 150                 155                 160

Arg Lys Trp Leu Gln Gln Met Met Leu Lys Lys Thr Leu Phe Asp Val
                165                 170                 175

Pro Phe Met His Leu Ser Cys Ser Ser Leu Lys Asn Tyr Lys Lys
                180                 185                 190

Met Glu Glu Lys Asn Gly Leu Leu Asn Trp Lys Met Leu Ile Ile Ser
                195                 200                 205

Trp Gly Met Ser Ser Leu Ile Arg Lys Glu Asn Leu Glu Xaa Phe Arg
                210                 215                 220

Tyr Ser Lys Ser Val Ala Pro Ser Ala Cys Glu Val Glu Lys Ile Ser
225                 230                 235                 240

Val Leu Gly Asp Thr Ile Gln Tyr Leu Lys Lys Leu Glu Ala Arg Val
                245                 250                 255
```

```
Glu Glu Leu Glu Ser Tyr Met Asp Thr Thr Ala Thr Gly Ala Arg Thr
            260                 265                 270

Arg Arg Lys Cys Pro Arg Val Gln Glu Gln Ile Ser Asp Asn Tyr Gly
            275                 280                 285

Pro Ser Asn Ile Tyr Met Gly Met Lys Lys Ser Arg Ile Asn Lys Arg
            290                 295                 300

Lys Ala Cys Asp Ile Asp Asp Ile Asp Thr Gly Leu Asp Ile Ile Val
305                 310                 315                 320

Ser

<210> SEQ ID NO 6
<211> LENGTH: 23
<212> TYPE: PRT
<213> ORGANISM: Lotus japonicus

<400> SEQUENCE: 6

Phe Arg Gly Ala Ala Thr Ala Pro Val Arg Met Ile Lys Glu Ala Leu
  1               5                  10                  15

Trp Lys Val Ser Gly Lys Ile
            20

<210> SEQ ID NO 7
<211> LENGTH: 648
<212> TYPE: PRT
<213> ORGANISM: Lotus uliginosis

<400> SEQUENCE: 7

Met Ala Val Gly Ser Pro Lys His Glu Lys Lys Met Gln Gln Lys
  1               5                  10                  15

Asn Leu Ser Ala Gln Leu Ala Val Ala Val Arg Ser Ile Gln Trp Ser
             20                  25                  30

Tyr Gly Ile Phe Trp Ala Pro Ser Thr Thr Gln Gln Arg Glu Leu Glu
         35                  40                  45

Trp Arg Asp Gly Phe Tyr Asn Gly Asp Ile Lys Thr Met Lys Thr Val
     50                  55                  60

Gln Thr Met Glu Thr Lys Ala Asp Lys Ile Gly Leu Gln Arg Ser Glu
 65                  70                  75                  80

Gln Leu Arg Glu Leu Tyr Arg Phe Leu Leu Glu Gly Glu Ala Asp Pro
                 85                  90                  95

Gln Ala Lys Arg Pro Ser Ala Ser Leu Ser Pro Glu Asp Leu Ser Asp
            100                 105                 110

Ser Glu Trp Tyr Tyr Leu Val Cys Met Ser Phe Val Phe Tyr Pro Asn
        115                 120                 125

Gln Ser Leu Pro Gly Lys Ala Leu Glu Ile Gly Glu Thr Val Trp Leu
    130                 135                 140

Cys Asn Ala Gln Gln Ala Asp Ser Lys Phe Phe Ser Arg Ser Leu Leu
145                 150                 155                 160

Ala Lys Ser Ala Ser Ile Gln Thr Val Val Cys Phe Pro Tyr Leu Gly
                165                 170                 175

Gly Val Ile Glu Ile Gly Thr Glu Val Val Ser Glu Asp Pro Asn Leu
            180                 185                 190

Ile Gln His Val Lys Thr Cys Phe Leu Glu Val Ser Lys Pro Thr Cys
        195                 200                 205

Ser Asp Lys Ser Ser Ser Ala His Asp Lys Pro His Asp Asp Asn Lys
    210                 215                 220
```

-continued

```
Tyr Pro Thr Cys Thr Lys Gly Asp His Glu Val Phe Asp Lys Met Pro
225                 230                 235                 240

Leu Glu Asn Ser Cys Ser Phe Ala Glu Leu Lys Phe Asp Glu Tyr
            245                 250                 255

Pro Gly Arg Glu Leu Gln Asp Asp Asn Asn Glu Asp Cys Asp Met
                260                 265                 270

Asp Gly Phe Ser Asp Gly Gly Tyr Asp His Tyr Glu Ser Met Ile Glu
            275                 280                 285

Gly Ile Asn Glu Gly Gly Ser Ser Gln Val His Phe Val Asn Asp Gly
290                 295                 300

Gly Glu Ile Asn Gly Ala Pro Asp Ser Leu Ser Ser Cys Asp Cys Met
305                 310                 315                 320

Ser Glu Ala Phe Glu Asn His Gly Lys Lys Asp Ser Ala Asn Val Thr
                325                 330                 335

Gln Ile Gln Gln Arg Glu Ile Ile Asp Cys Asp Asp His Ser Lys Ser
            340                 345                 350

Ser Ser Leu Asp Ile Gly Ala Asp Glu Asp Leu Tyr Tyr Thr Lys Thr
        355                 360                 365

Leu Cys Ala Ile Leu Gly Asn Ser Ser Ser Phe Ala Gln Asn Leu Cys
370                 375                 380

Ala Ser Lys Ser Ser Phe Val Lys Trp Lys Lys Gly Gly Val Ser Glu
385                 390                 395                 400

Arg Lys Arg Pro Trp Leu Gln Gln Met Met Leu Lys Lys Thr Leu Phe
                405                 410                 415

Asp Val Pro Phe Met His Leu Ser Cys Ser Ser Leu Lys Leu Gln Lys
            420                 425                 430

Glu Asn Gly Arg Lys Glu Trp Thr Ser Lys Leu Glu Asn Ala Asp Asn
        435                 440                 445

Phe Met Gly Asn Val Phe Ser Asp Lys Lys Arg Glu Ser Arg Asn Ile
    450                 455                 460

Gln Val Leu Lys Ser Val Ala Pro Ser Ala Cys Glu Val Glu Lys Ile
465                 470                 475                 480

Ser Val Leu Gly Gly Thr Ile Lys Tyr Leu Lys Asn Leu Glu Ala Arg
                485                 490                 495

Val Glu Glu Leu Glu Ser Tyr Met Asp Thr Thr Ala Thr Gly Ala Arg
            500                 505                 510

Thr Lys Arg Lys Cys Pro Asp Val Leu Glu Gln Ile Ser Asp Asn Tyr
        515                 520                 525

Gly Pro Ser Asn Ile Tyr Met Gly Met Lys Lys Pro Met Ile Asn Lys
    530                 535                 540

Arg Lys Ala Cys Asp Ile Asp Asn Ile Asp Thr Gly Leu Asp Ile Ile
545                 550                 555                 560

Val Ser Glu Glu Asp Lys Pro Leu Asp Val Lys Val Asn Met Lys Glu
                565                 570                 575

Glu Glu Val Leu Ile Glu Met Lys Cys Pro Tyr Arg Glu Tyr Ile Leu
            580                 585                 590

Tyr Asp Ile Met Asp Ala Ile Asn Asn Leu His Ile Asp Ala His Tyr
        595                 600                 605

Val Asp Ser Ser Thr Ala Asp Gly Val Leu Thr Phe Lys Leu Lys Ser
    610                 615                 620

Lys Phe Arg Gly Ala Ala Thr Ala Pro Val Arg Met Ile Lys Glu Ala
625                 630                 635                 640

Leu Trp Lys Val Ser Gly Lys Ile
```

<210> SEQ ID NO 8
<211> LENGTH: 2660
<212> TYPE: DNA
<213> ORGANISM: Lotus corniculatus
<220> FEATURE:
<221> NAME/KEY: misc_feature
<222> LOCATION: (1)...(2660)
<223> OTHER INFORMATION: n = A,T,C or G

<400> SEQUENCE: 8

| | | | | | |
|---|---|---|---|---|---|
| tagatgttgg | aatggaggga | tgggttctac | aatggagaca | ttaagacaat | gaagacagtg | 60 |
| caaaccatgg | aaactaaggc | tgataaaata | ggcctgcaga | ggagtgaaca | actgagagaa | 120 |
| ctatacaagt | ttcttcttgt | aggtgaagct | gacccactag | ctaaaagacc | ttctgcttca | 180 |
| ttatctccag | aggatctctc | agattcagag | tggtattact | tggtttgcat | gtcctttgtg | 240 |
| ttctacccca | accaaggta | ccatatatgc | tctaatttca | tttaattcat | ataagggatt | 300 |
| aattaatgtt | ttgtttcttt | atcaattttt | ctagttttt | atatttaact | aagttgggtt | 360 |
| tttcttttct | tctcacagtt | tgcctggaaa | agcactagaa | actggtgaaa | cagtgtggct | 420 |
| atgcaatgct | cagcaggcag | atagtaaatt | tttctctcgt | tctttgctag | caaaggttgg | 480 |
| attttattca | taaatttgat | attttggttt | tcatattata | tgatgtacgg | agaatgtaag | 540 |
| gttgatgata | taatatgtgg | tccaaccttg | gatttggctc | agtggggtaa | acatcaatga | 600 |
| gttttatgat | gctcaatttc | ttccaataag | cattgagcaa | gttgttctct | agaagaaaga | 660 |
| aatatctttc | gcagtctttg | attatatcaa | atgttggtca | aaaagttctt | acgactagat | 720 |
| aaaatgtaag | ctaacttgac | caacatttaa | cacaattagg | tccatgagga | ttggctatct | 780 |
| tttaaaagac | taacttgncc | acggttacac | tttcaggaat | gaaaatggcc | attaactcga | 840 |
| tttttaaaat | ttactagaat | ttaatttca | tatagaaatt | actatccata | aattttgggt | 900 |
| tttaattcca | tycccacytc | mcyttatctt | ctatttcatt | ttcggaaacc | tttkggtttc | 960 |
| cnatttcccc | anattttcc | ttatcgcncc | ncttatccat | accattatta | atttattatt | 1020 |
| tttttccatn | cggtatgact | gacctccaat | ccnttttcca | ccaattttc | tttttctttt | 1080 |
| tccatgtgga | catgggtttc | aattgctgta | tccagagtgc | ctctattcag | gtatgacatt | 1140 |
| ctctctacac | ccttttctat | ctaaggttaa | aaatggtatt | ttgttagtcg | gcatttggtt | 1200 |
| aaaataactt | aattaagtgc | ttatgagctt | aaaatataat | tgaagtgctt | atgacgacga | 1260 |
| gcgattatga | cancaagtta | catatatttt | gacaaaccta | tggaaataag | ctaaaattat | 1320 |
| ttgaaaaact | tattgaaata | tgctcaaaat | gtattgcaag | taaacccta | ttcataagct | 1380 |
| aatttgaatt | tctatgaaa | ataagtttaa | ataacttat | agataggcca | aaagctattt | 1440 |
| aaatattttc | tttcaactac | ttgtataagt | gtttgtgcta | ttccacagaa | actaacttga | 1500 |
| agttggtggt | aaatattggg | gttatttggg | attgtgatta | tgtcttaact | aaaaaggtga | 1560 |
| aacaaaagta | aaatgcaaaa | gtgagctatc | ttcaaggcaa | gggctgagta | tagatattgt | 1620 |
| gatttgtacc | ctatcccata | ttctaacttt | accttatgac | agaagcatag | atattaacat | 1680 |
| tcatactgtg | tggtgtgtgc | taaaacctgt | ttttcagaca | gtggtgtgtt | ttccctatct | 1740 |
| tggaggtgtc | attgagatag | gaacaactga | agnnnnnnta | aaatgccctt | ggagaactca | 1800 |
| tgttcctttg | cagaagaact | caaatttgat | gaatatcctg | gcaggagtt | acaagatgat | 1860 |
| gataacaatg | aagattgtga | catggatgga | ttctctgatg | gtggttgtga | tcattatgaa | 1920 |
| tccatgatag | ggggcatcaa | cgagggtggt | tcttctcaag | ttcattttgt | gaatgaaggt | 1980 |

-continued

```
ggtgacatca atggtgcccc agattcctct agttcttgtg attgtaggtc tgaggcttct    2040
gagaaccatg gtaagaagga ttctaaaaat gtaatccaaa ttcaacaaaa ggagcttcaa    2100
gactgtgatg ataactcaaa aagtagctct ttggatattg gagctgatga agatttgtac    2160
tacacaagaa ctctctgtgc tgttctggga aattcatcaa gttttgcaca aatctatgt     2220 gcaagtaaat ctagttttgt gaaatggaat aagggaggag tttctgaaag gaagtggccg    2280
cggttgcaac aaatgatgtt aagaagact  ttgtttgatg tcccttttat gcacctaagt    2340
tgctcctctc tcaaattaca aaagaaaat  ggaagaaaag aatggncttc taaattggaa    2400
aatgctgata atttcatggg gaatgtcttc tctgataaga aaagagaatc tagaaacatt    2460
caggtactca atctgtggc  tcctttctgc atgtgaggta ttggacttat catctgctga    2520
nattaatggt atcccttcat gantggatgn tggttggaaa tttgcatgct acaatgctta    2580
nnnnnnccta tggccccngt aatatttaca tgggaatgaa aanatctagg ataaacaaga    2640
gnaaggcttg tgatattgat                                                2660
```

<210> SEQ ID NO 9
<211> LENGTH: 144
<212> TYPE: PRT
<213> ORGANISM: Lotus corniculatus
<220> FEATURE:
<221> NAME/KEY: VARIANT
<222> LOCATION: (1)...(144)
<223> OTHER INFORMATION: Xaa = Any Amino Acid

<400> SEQUENCE: 9

```
Leu Glu Trp Arg Asp Gln Phe Tyr Asn Gly Asp Ile Lys Thr Met Lys
 1               5                  10                  15

Thr Val Gln Thr Met Glu Thr Lys Ala Asp Lys Ile Gly Leu Gln Arg
            20                  25                  30

Ser Glu Gln Leu Arg Glu Leu Tyr Lys Phe Leu Leu Val Gly Glu Ala
        35                  40                  45

Asp Pro Leu Ala Lys Arg Pro Ser Ala Ser Leu Ser Pro Glu Asp Leu
    50                  55                  60

Ser Asp Ser Glu Trp Tyr Tyr Leu Val Cys Met Ser Phe Val Phe Tyr
65                  70                  75                  80

Pro Asn Gln Ser Leu Pro Gly Lys Ala Leu Glu Thr Gly Glu Thr Val
                85                  90                  95

Trp Leu Cys Asn Ala Gln Gln Ala Asp Ser Lys Phe Phe Ser Arg Ser
            100                 105                 110

Leu Leu Ala Lys Xaa Xaa Xaa Xaa Xaa Xaa Gln Thr Val Val Cys Phe
        115                 120                 125

Pro Tyr Leu Gly Gly Val Ile Glu Ile Gly Gly Thr Glu Xaa Xaa Xaa
    130                 135                 140
```

<210> SEQ ID NO 10
<211> LENGTH: 233
<212> TYPE: PRT
<213> ORGANISM: Lotus corniculatus

<400> SEQUENCE: 10

```
Leu Glu Asn Ser Cys Ser Phe Ala Glu Glu Leu Lys Phe Asp Glu Tyr
 1               5                  10                  15

Pro Gly Arg Glu Leu Gln Asp Asp Asn Asn Glu Asp Cys Asp Met
            20                  25                  30

Asp Gly Phe Ser Asp Gly Gly Cys Asp His Tyr Glu Ser Met Ile Gly
```

```
            35                  40                  45
Gly Ile Asn Glu Gly Ser Ser Gln Val His Phe Val Asn Glu Gly Gly
 50                  55                  60

Asp Ile Asn Gly Ala Pro Asp Ser Ser Ser Cys Ser Cys Arg Ser
 65                  70                  75                  80

Glu Ala Ser Glu Asn His Gly Lys Lys Asp Ser Lys Asn Val Ile Gln
                 85                  90                  95

Ile Gln Gln Lys Glu Leu Gln Asp Cys Asp Asn Ser Lys Ser Ser
            100                 105                 110

Ser Leu Asp Ile Gly Ala Asp Glu Asp Leu Tyr Tyr Thr Arg Thr Leu
            115                 120                 125

Cys Ala Val Leu Gly Asn Ser Ser Phe Ala Gln Asn Leu Cys Ala
130                 135                 140

Ser Lys Ser Ser Phe Val Lys Trp Asn Lys Gly Val Ser Glu Arg
145                 150                 155                 160

Lys Trp Leu Gln Gln Met Met Leu Lys Lys Thr Leu Phe Asp Val Pro
                165                 170                 175

Phe Met His Leu Ser Cys Ser Ser Leu Lys Tyr Lys Lys Lys Met Glu
            180                 185                 190

Glu Lys Asn Gly Leu Leu Asn Gln Lys Met Leu Ile Ile Ser Trp Gly
            195                 200                 205

Met Ser Ser Leu Ile Arg Lys Glu Asn Leu Glu Thr Phe Arg Tyr Ser
210                 215                 220

Asn Leu Trp Leu Leu Ser Ala Cys Glu
225                 230

<210> SEQ ID NO 11
<211> LENGTH: 29
<212> TYPE: DNA
<213> ORGANISM: Artificial Sequence
<220> FEATURE:
<223> OTHER INFORMATION: A primer
<220> FEATURE:
<221> NAME/KEY: misc_feature
<222> LOCATION: (1)...(29)
<223> OTHER INFORMATION: n = A,T,C or G

<400> SEQUENCE: 11
gggtgctnac gtcgacggan gggttctac                                    29

<210> SEQ ID NO 12
<211> LENGTH: 29
<212> TYPE: DNA
<213> ORGANISM: Artificial Sequence
<220> FEATURE:
<223> OTHER INFORMATION: A primer
<220> FEATURE:
<221> NAME/KEY: misc_feature
<222> LOCATION: (1)...(29)
<223> OTHER INFORMATION: n = A,T,C or G

<400> SEQUENCE: 12
gggatccaga cnantgtctg aatngacgc                                    29

<210> SEQ ID NO 13
<211> LENGTH: 27
<212> TYPE: DNA
<213> ORGANISM: Artificial Sequence
<220> FEATURE:
<223> OTHER INFORMATION: A primer
<220> FEATURE:
<221> NAME/KEY: misc_feature
```

```
<222> LOCATION: (1)...(27)
<223> OTHER INFORMATION: n = A,T,C or G

<400> SEQUENCE: 13
tccggnacct gatcagtagt accaagc                                              27

<210> SEQ ID NO 14
<211> LENGTH: 24
<212> TYPE: DNA
<213> ORGANISM: Artificial Sequence
<220> FEATURE:
<223> OTHER INFORMATION: A primer

<400> SEQUENCE: 14
cctattttat cagccttagt ttcc                                                 24

<210> SEQ ID NO 15
<211> LENGTH: 25
<212> TYPE: DNA
<213> ORGANISM: Artificial Sequence
<220> FEATURE:
<223> OTHER INFORMATION: A primer

<400> SEQUENCE: 15
gtcttaatgt ctccattgta gaacc                                                25

<210> SEQ ID NO 16
<211> LENGTH: 24
<212> TYPE: DNA
<213> ORGANISM: Artificial Sequence
<220> FEATURE:
<223> OTHER INFORMATION: A primer

<400> SEQUENCE: 16
ggatctctca gattcagagt ggta                                                 24

<210> SEQ ID NO 17
<211> LENGTH: 20
<212> TYPE: DNA
<213> ORGANISM: Artificial Sequence
<220> FEATURE:
<223> OTHER INFORMATION: A primer

<400> SEQUENCE: 17
tggtttgcat gtcctttgtg                                                      20

<210> SEQ ID NO 18
<211> LENGTH: 27
<212> TYPE: DNA
<213> ORGANISM: Artificial Sequence
<220> FEATURE:
<223> OTHER INFORMATION: A primer

<400> SEQUENCE: 18
ggttctacaa tggagacatt aagacaa                                              27

<210> SEQ ID NO 19
<211> LENGTH: 22
<212> TYPE: DNA
<213> ORGANISM: Artificial Sequence
<220> FEATURE:
<223> OTHER INFORMATION: A primer

<400> SEQUENCE: 19
tcttccttac agaaactcct cc                                                   22
```

```
<210> SEQ ID NO 20
<211> LENGTH: 22
<212> TYPE: DNA
<213> ORGANISM: Artificial Sequence
<220> FEATURE:
<223> OTHER INFORMATION: A primer

<400> SEQUENCE: 20
atgaagattg tgacatggat gg                                                  22

<210> SEQ ID NO 21
<211> LENGTH: 24
<212> TYPE: DNA
<213> ORGANISM: Artificial Sequence
<220> FEATURE:
<223> OTHER INFORMATION: A primer

<400> SEQUENCE: 21
atcaatatca caagccttcc tctt                                                24
```